United States Patent
Yonemura et al.

(10) Patent No.: US 9,874,504 B2
(45) Date of Patent: Jan. 23, 2018

(54) METAL SHEET BENDING FRACTURE DETERMINATION METHOD AND RECORDING MEDIUM

(71) Applicant: NIPPON STEEL & SUMITOMO METAL CORPORATION, Tokyo (JP)

(72) Inventors: Shigeru Yonemura, Tokyo (JP); Takuya Kuwayama, Tokyo (JP); Akihiro Uenishi, Tokyo (JP); Toshiyuki Niwa, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 19 days.

(21) Appl. No.: 14/897,057

(22) PCT Filed: Jun. 26, 2014

(86) PCT No.: PCT/JP2014/067063
§ 371 (c)(1),
(2) Date: Dec. 9, 2015

(87) PCT Pub. No.: WO2014/208697
PCT Pub. Date: Dec. 31, 2014

(65) Prior Publication Data
US 2016/0161382 A1    Jun. 9, 2016

(30) Foreign Application Priority Data

Jun. 26, 2013  (JP) .................................. 2013-134199

(51) Int. Cl.
*G01N 3/20*      (2006.01)
*G06F 17/50*     (2006.01)

(52) U.S. Cl.
CPC .......... *G01N 3/20* (2013.01); *G06F 17/5009* (2013.01); *G06F 17/5018* (2013.01);
(Continued)

(58) Field of Classification Search
CPC ............. G01N 3/20; G01N 2203/0212; G01N 2203/0214; G06F 17/5018; G06F 2217/42; G06F 2217/16
(Continued)

(56) References Cited

U.S. PATENT DOCUMENTS 8,606,532 B2 * 12/2013 Hiwatashi ........... G01M 5/0033
                                                                702/42
8,990,028 B2 *  3/2015 Yonemura ................ G01N 3/00
                                                                702/35
(Continued)

FOREIGN PATENT DOCUMENTS

JP     2011-141237     7/2011
JP     2012-166251     9/2012
(Continued)

OTHER PUBLICATIONS

Stoughton, Thomas "A general forming limit criterion for sheet metal forming" International Journal of Mechanical Sciences. vol. 42 (2000), pp. 1-27. Accessed [Online] Mar. 26, 2017. <http://www.sciencedirect.com/science/article/pii/S0020740398001131>.*

Zadpoor et al. "Fracture in bending—The straining limits of monlithic sheets and machined tailor-made blanks" Materials and Design. vol. 32 (2011), pp. 1229-1241. Accessed [Online] Mar. 26, 2017. <http://www.sciencedirect.com/science/article/pii/S0261306910005832>.*

(Continued)

*Primary Examiner* — Jonathan Dunlap
(74) *Attorney, Agent, or Firm* — Birch, Stewart, Kolasch & Birch, LLP

(57) ABSTRACT

A bending fracture limit stress is calculated for each of (bend radius at sheet thickness center of a metal sheet)/(initial sheet thickness of the metal sheet); a fracture limit curve and a fracture limit stress are calculated from work hardening characteristics; a fracture limit curve corresponding to (the metal sheet bend radius at sheet thickness center)/(the initial sheet thickness of the metal sheet) is calculated; a corresponding fracture limit stress is calculated from stress of the element subject to determination and the fracture limit curve; a risk ratio that is a ratio between the stress of the (Continued)

element subject to determination and the fracture limit stress is computed; and performing fracture determination for the element subject to determination based on the risk ratio.

4 Claims, 16 Drawing Sheets

(52) U.S. Cl.
CPC ............... *G01N 2203/0212* (2013.01); *G01N 2203/0214* (2013.01); *G06F 2217/16* (2013.01); *G06F 2217/42* (2013.01)

(58) Field of Classification Search
USPC ........ 702/41.42; 73/760, 788, 804, 849, 851
See application file for complete search history.

(56) References Cited

U.S. PATENT DOCUMENTS

| | | | | |
|---|---|---|---|---|
| 2009/0177417 | A1* | 7/2009 | Yonemura | G01N 3/00 702/42 |
| 2013/0000415 | A1* | 1/2013 | Yoshida | B23K 11/11 73/827 |
| 2013/0006543 | A1* | 1/2013 | Hiwatashi | G01M 5/0033 702/42 |

FOREIGN PATENT DOCUMENTS

| | | |
|---|---|---|
| JP | 2007-232715 | 9/2013 |
| WO | 2013157062 | 10/2013 |
| WO | 2013157063 | 10/2013 |

OTHER PUBLICATIONS

Morales-Palma et al. "Assessment of the effect of the through-thickness strain/stress gradient on the formability of stretch-bend metal sheet" Materials and Design. vol. 50 (2013) 798-809. Accessed [Online] Mar. 26, 2017. <http://www.sciencedirect.com/science/article/pii/S026130691300294X>.*

Jain et al. "Fracture limit prediction using ductile fracture criteria for forming of an automotive aluminum sheet" International Journal of Mechanical Sciences. vol. 41 (1999), pp. 1273-1288. Accessed [Online] Mar. 26, 2017. <http://www.sciencedirect.com/science/article/pii/S0020740398000708>.*

International Search Report dated Sep. 30, 2014 issued in corresponding International Application No. PCT/JP2014/067063.

Extended European Search Report for European Application No. 14818203.3, dated Feb. 15, 2017.

Morales-Palma et al., "Assessment of the Effect of the Through-Thickness Strain/Stress Gradient on the Formability of Stretch-Bend Metal Sheets," Materials and Design, vol. 50, 2013 (published online Apr. 4, 2013), pp. 798-809.

Oh et al., "Finite Element Analysis of Plane-Strain Sheet Bending," International Journal of Mechanical Sciences, vol. 22, No. 9, Jan. 1, 1980, pp. 583-594 (12 pages total).

Stoughton et al., "A New Approach for Failure Criterion for Sheet Metals," International Journal of Plasticity, vol. 27, 2011 (published online Jul. 15, 2010), pp. 440-459.

Wang et al., "Mathematical Modeling of Plane-Strain Bending of Sheet and Plate," Journal of Materials Processing Technology, vol. 39, Nos. 3-4, Nov. 1, 1993, pp. 279-304.

* cited by examiner

SHEET THICKNESS DIRECTION STRAIN
DISTRIBUTION AT BEND

FIG.15
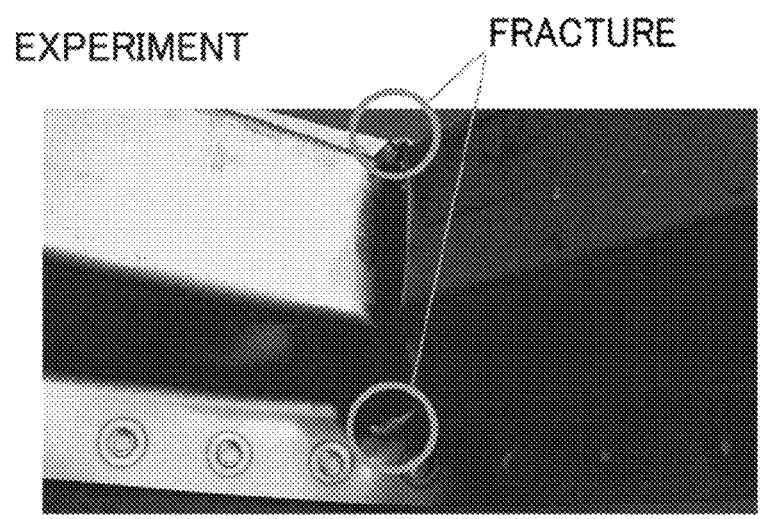
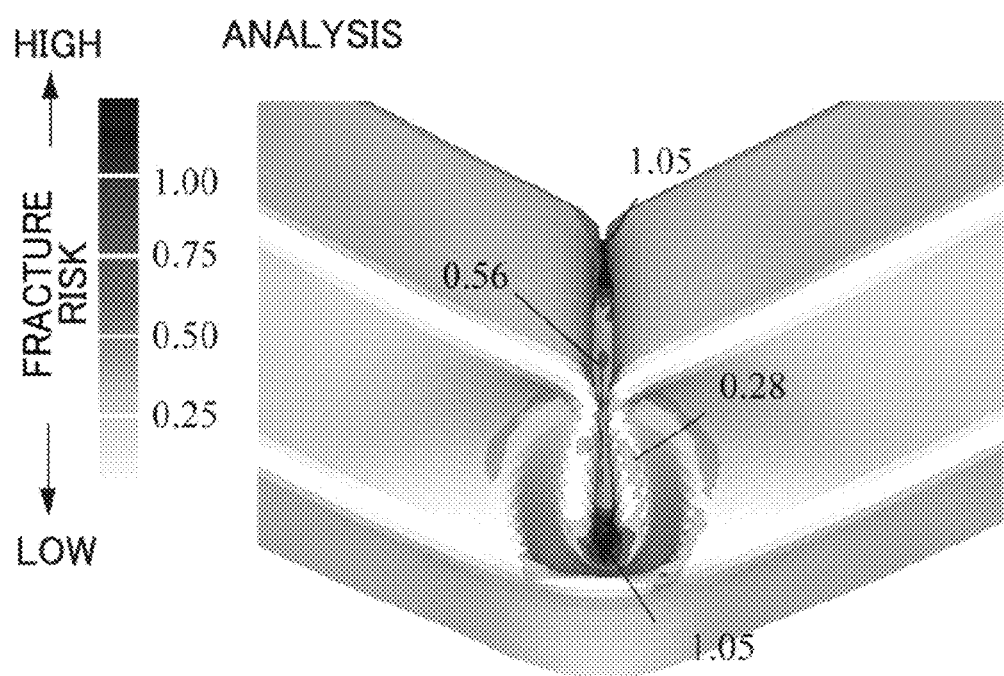

METAL SHEET BENDING FRACTURE
DETERMINATION METHOD AND
RECORDING MEDIUM

CROSS-REFERENCE TO RELATED
APPLICATIONS

This application is a national stage application of International Application No. PCT/JP2014/067063, filed Jun. 26, 2014, which is incorporated herein by reference in its entirety, and which claims priority to Japanese Patent Application No. 2013-134199, filed on Jun. 26, 2013.

TECHNICAL FIELD

The present invention relates to a metal sheet bending fracture determination method, program, and recording medium. More precisely, the present invention relates to a metal sheet bending fracture determination method, program, and recording medium employed for determining risk of bending fracture in a metal sheet in a forming process in which a vehicle body component of an automobile is press worked, or in a crash deformation process of a vehicle body component of an automobile.

BACKGROUND ART

Application of high strength steel sheet to automobile bodies has recently been progressing rapidly due to demands for crash safety and weight reduction. Employing high strength steel sheet in automobile bodies enables the energy absorbed in a crash to be increased and buckling strength to be increased, without increasing sheet thickness. However, there is a concern that the steel sheet may fracture during press forming or crash deformation, due to the ductility and bendability of steel sheet decreasing along with increasing strength of the steel sheet. In order to determine the state of the steel sheet during press forming and crash deformation, there is an increasing need to determine steel sheet fracture with high precision using finite element methods.

The use of sheet thickness reduction ratios or forming limit diagrams (FLDs) is known for evaluating the formability and the amount of leeway with respect to fracture during crash performance evaluation.

FIG. 1 illustrates an example of a FLD in a strain space from uniaxial deformation to plane strain deformation, and from plane strain deformation uniform biaxial deformation.

As illustrated in this drawing, the FLD is a diagram illustrating a relationship between the major strain and minor strain that give a fracture limit. Brief explanation follows regarding experimental measurement methods for FLDs. First, a metal sheet, having a circular or lattice pattern drawn on the surface thereof, by etching or the like, is fractured by hydraulic forming or stretch forming with a rigid tool. Next, the fracture limit strain is determined from the amount of deformation in the pattern on the surface of the fractured metal sheet. Load is applied to the metal sheet so as to change an in-plane strain ratio, and a fracture limit curve is obtained by plotting the fracture limit strain for each strain ratio.

Combined application of Hill's criterion and Swift's one, the Marciniak-Kuczynski model, the Storen-Rice model, and the like are known, as theoretically predicting FLDs. In ductile fracture of materials, deformation caused by localized necking is generated at localized positions. The criterion is often considered identical to the localized necking generation limit due to the generation of localized necking causing materials to fracture within a very short time. Therefore, the predicted criterion is often treated as a plastic instability phenomenon. In the conventional fracture prediction method described in Japanese Patent Application Laid-Open (JP-A) No. 2012-33039, risk of fracture is predicted by comparing positional relationships between a fracture limit curve and a strain state for each element obtained from simulation by a finite element method. Namely, it is determined that there is a fracture or that there is a high risk of fracture when strain in a deformation process obtained from simulation reaches a limiting strain defined by the fracture limit curve.

SUMMARY OF INVENTION

Technical Problem

As described above, FLDs obtained from experiment and theoretical predictions pertain to phenomena in which material separates in a state of uniform stress, or to phenomena in which localized necking arises. However, in the case of bending, there is a large strain gradient from the outside to the inside of the bend.

FIG. 2 is a diagram explaining localized necking in a state of uniform stress. FIG. 3 is a diagram explaining a strain gradient in the sheet thickness direction of a bend portion.

As illustrated in FIG. 3, at a bend portion, in cases in which the fracture conditions have been reached at the bend outside in a state of uniform stress, the fracture conditions will not have been reached at the bend inside due to the large strain gradient from the bend outside toward the bend inside. Even in cases in which the fracture conditions have been reached at the bend outside, sometimes a plastically unstable state does not arise and fracture of the material overall does not result due to the supporting effect of the bend inside.

A condition in which the fracture conditions have not been reached at the bend inside even though the fracture conditions have been reached at the bend outside is a characteristic of a bend portion, and the occurrence of localized necking at a bend portion differs from the occurrence of localized necking in a state of uniform stress, such as the uniaxial tension, stretching, or deep drawing as illustrated in FIG. 2. Although the occurrence of localized necking at a bend portion differs from the occurrence of localized necking in a state of uniform stress, there is no known method based on bend portion fracture for determining bending fracture by forming analysis or crash analysis.

An object of the present invention is to provide a metal sheet bending fracture determination method capable of quantitatively determining risk of bending fracture from results of forming analysis or crash analysis by a finite element method, irrespective of characteristics of the metal forming the metal sheet and the load state in cases in which the metal sheet is bent. Another object of the present invention is to provide a program of a metal sheet bending fracture determination method capable of quantitatively determining risk of bending fracture, and a recording medium storing the program.

Solution to Problem

A first aspect of the present invention is a metal sheet bending fracture determination method including: calculating a bending fracture limit stress for each of (bend radius at sheet thickness center of a metal sheet)/(initial sheet thickness of the metal sheet); calculating a fracture limit curve of a uniform deformation state in space of stresses under the assumption of static strain rate and calculating a fracture limit stress under plane strain deformation, from work hardening characteristics obtained by uniaxial tensile testing of a material configuring the metal sheet; determining a ratio between the bending fracture limit stress corresponding to (the metal sheet bend radius at sheet thickness center)/(the initial sheet thickness of the metal sheet) of an element subject to determination in the metal sheet and the fracture limit stress under plane strain deformation, and calculating a fracture limit curve corresponding to (the metal sheet bend radius at sheet thickness center)/(the initial sheet thickness of the metal sheet) by multiplying a stress component of the fracture limit curve in the uniform deformation state by the ratio between the bending fracture limit stress corresponding to (the metal sheet bend radius at sheet thickness center)/(the initial sheet thickness of the metal sheet) of the element subject to determination and the fracture limit stress under plane strain deformation; calculating a corresponding fracture limit stress from stress of the element subject to determination and the fracture limit curve corresponding to (the metal sheet bend radius at sheet thickness center)/(the initial sheet thickness of the metal sheet); computing a risk ratio that is a ratio between the stress of the element subject to determination and the fracture limit stress calculated from the stress of the element subject to determination and the fracture limit curve corresponding to (the metal sheet bend radius at sheet thickness center)/(the initial sheet thickness of the metal sheet); and performing fracture determination for the element subject to determination based on the risk ratio.

According to the above aspect, fracture determination is performed for elements subject to determination in the metal sheet based on the risk ratio obtained by the above calculation. Namely, the metal sheet can be determined to have fractured in cases in which the risk ratio has reached 1.0 or more, and determination can be made that the amount of leeway until the metal sheet fractures is less the closer the risk ratio is to 1.0. Moreover, in the present invention, the fracture limit curve is computed by correcting the fracture limit curve obtained from uniaxial tensile testing with the above ratio, and the fracture limit stress of the element subject to determination is determined based on the corrected fracture limit curve. This thereby enables higher precision fracture determination to be performed on metal sheets than in cases in which the fracture limit stress of the element subject to determination is determined based on the fracture limit curve obtained from uniaxial tensile testing alone.

Advantageous Effects of Invention

The present invention has the excellent advantageous effect of enabling risk of bending fracture to be quantitatively determined from results of forming analysis or crash analysis by a finite element method.

BRIEF DESCRIPTION OF DRAWINGS

FIG. 15 is a diagram illustrating fracture risk found using the present invention for the three-point crash analysis employed in the examples of the present invention, displaying isopleths as contours.

DESCRIPTION OF EMBODIMENTS

Figure 1:
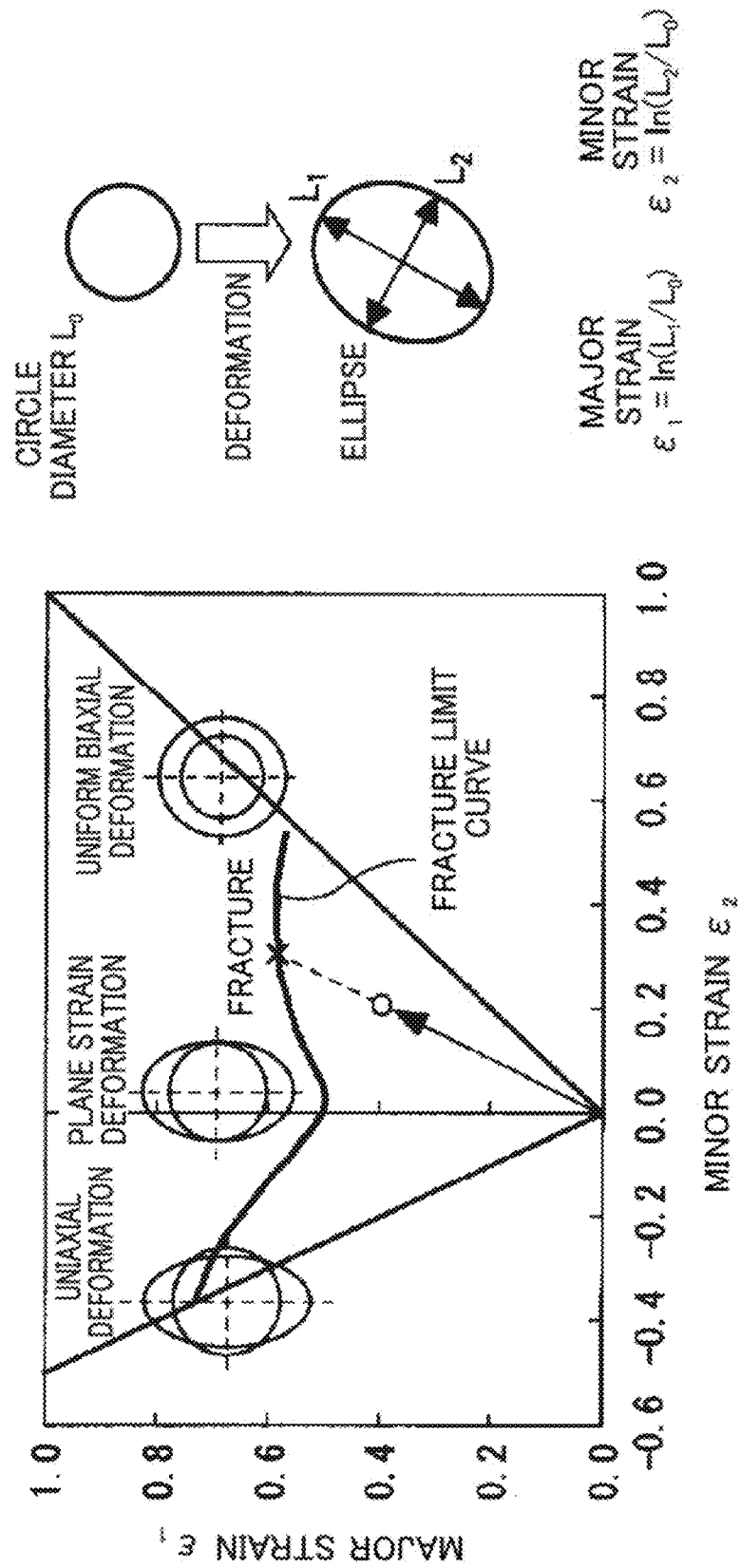
FIG. 1 is a diagram illustrating an example of a forming limit diagram.
Figure 2:
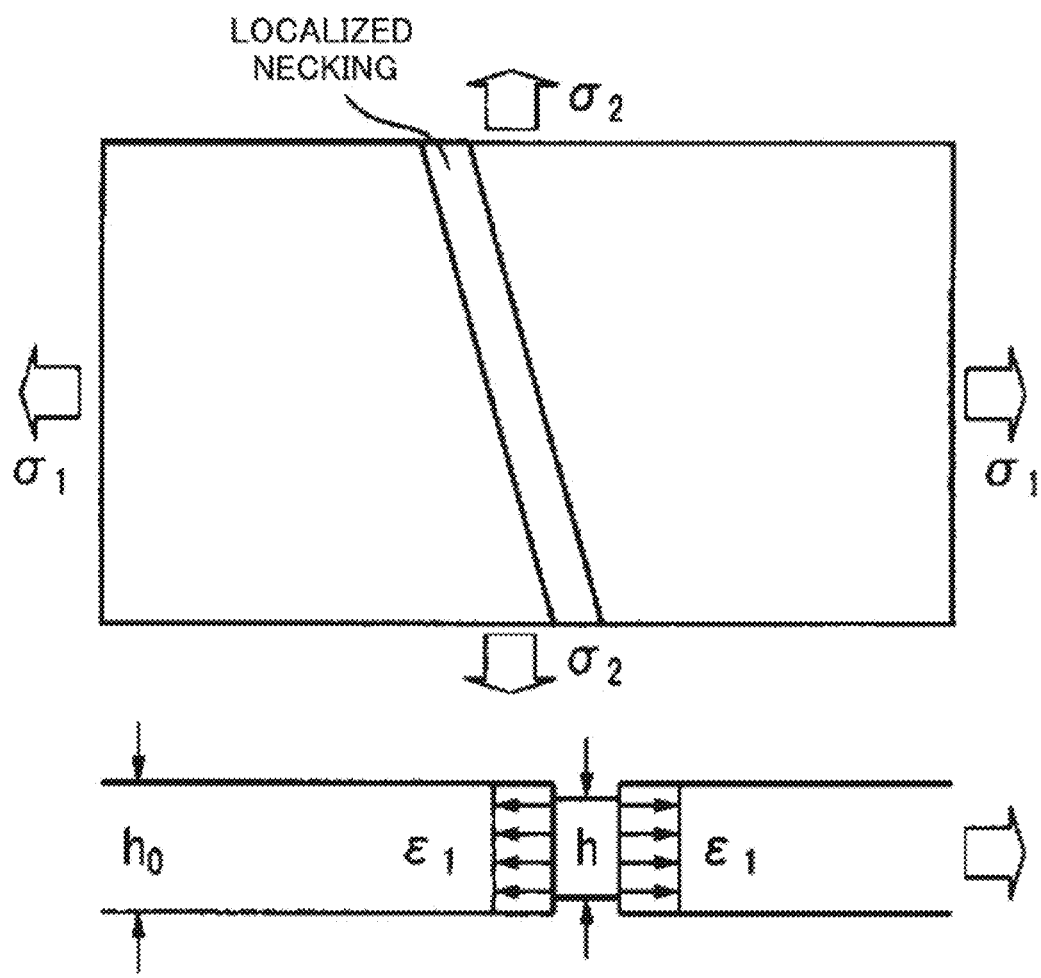
FIG. 2 is a diagram explaining localized necking in a uniform stress state.
Figure 3:
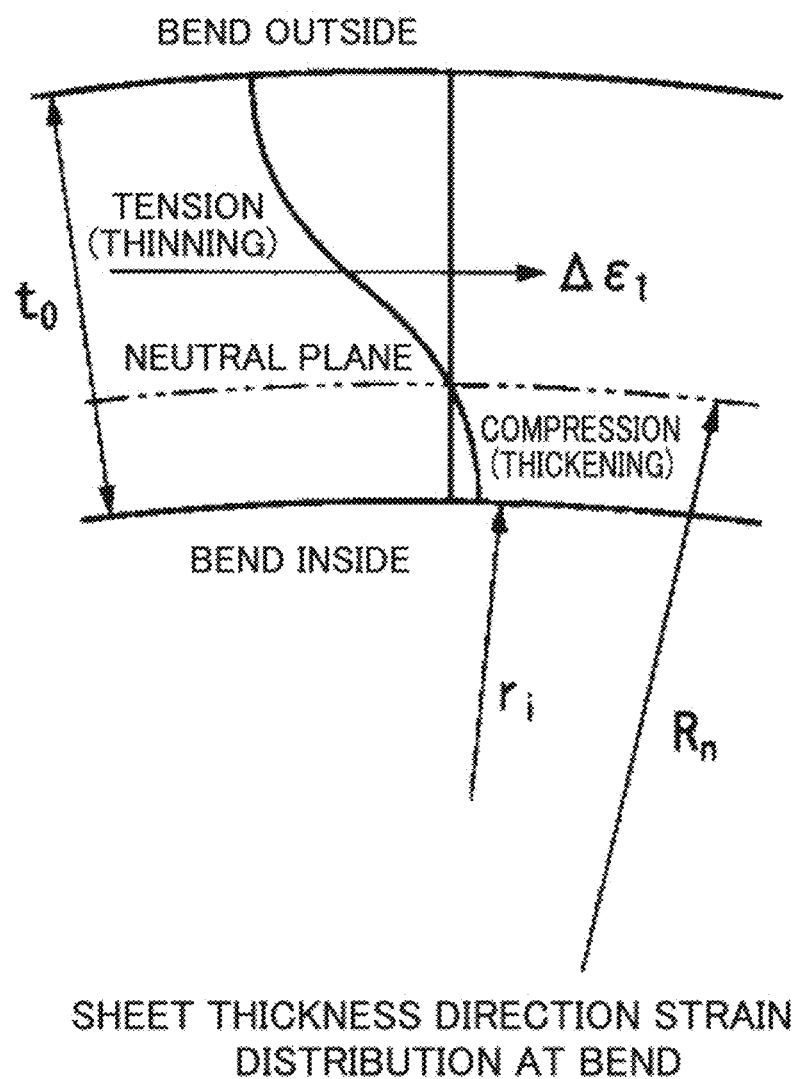
FIG. 3 is a diagram explaining a sheet thickness direction strain gradient at a bend portion.

Detailed explanation follows regarding an exemplary embodiment of the present invention, with reference to the drawings.

Fundamental Idea

In cases in which bending deformation occurs in metal sheets made from a metal material, peripheral direction tensile stress in the material decreases, and radial direction compressive stress in the material increases, from the bend outside toward the inside, and, as bending progresses, the magnitude of these stresses and the stress state changes. However, localized necking conditions that apply for uniform distributions cannot be applied due to the stress and strain occurring with bending not being uniformly distributed in the sheet thickness direction. Since localized necking conditions corresponding to a uniform distribution cannot be applied to fracture determination in a bend portion, it has hitherto been common to determine fracture at bend portions by using forming simulation or crash simulation, however this cannot be said to give sufficient reliability in practice.

Investigations have therefore been made into bending fracture determination methods capable of determining the risk of bending fracture from results of forming analysis and crash analysis using a finite element method in press forming or crash deformation incurring bending deformation having a strain gradient in the sheet thickness direction.

Mechanisms by which bending fracture occurs are broadly divided by fracture mode into two fracture modes. The first fracture mode is a fracture mode in which cracking occurs on the bend outside surface without the appearance of obvious localized necking. The second fracture mode is a fracture mode in which fracture occurs after pronounced sheet thickness reduction (localized necking) has been observed at a bend leading end portion even though cracking does not occur at the bend outside. In order to predict bending fracture that occurs in these two different fracture modes, the inventors have developed a metal sheet fracture determination method, including: comparing (1) a first risk ratio having, as a criterion, a bending-surface limit stress that is a bending-surface limit strain converted into stress, and a second risk ratio having, as a criterion, bending fracture limit curves in space of stresses that are obtained by (2)-1 finding fracture limit stresses for respective bending radii from a theoretical solution for the relationship between stress of plane strain stretch bending and strain, finding stretch bending fracture limit stress under plane strain deformation for respective (bending radius R at sheet thickness center)/(initial sheet thickness $t_0$) of elements from strain generating conditions ($d\sigma_1/d\epsilon_1 = \sigma_1$), which will be described in detail later, (2)-2 finding a criterion in space of stresses, from work hardening characteristics obtained from uniaxial tensile tests on a material, under the assumption of static strain rates, and (2)-3 offsetting criteria collected in (2)-2 under plane strain deformation, to carry out determination of fracture in sheet steel based on the larger risk ratio from either the first risk ratio or the second risk ratio. First, explanation follows regarding the first risk ratio, and then explanation follows regarding the second risk ratio. Note that (bending radius R)/(initial sheet thickness $t_0$) is simply referred to as bending amount $R/t_0$ hereafter.

First Risk Ratio

Figure 4:
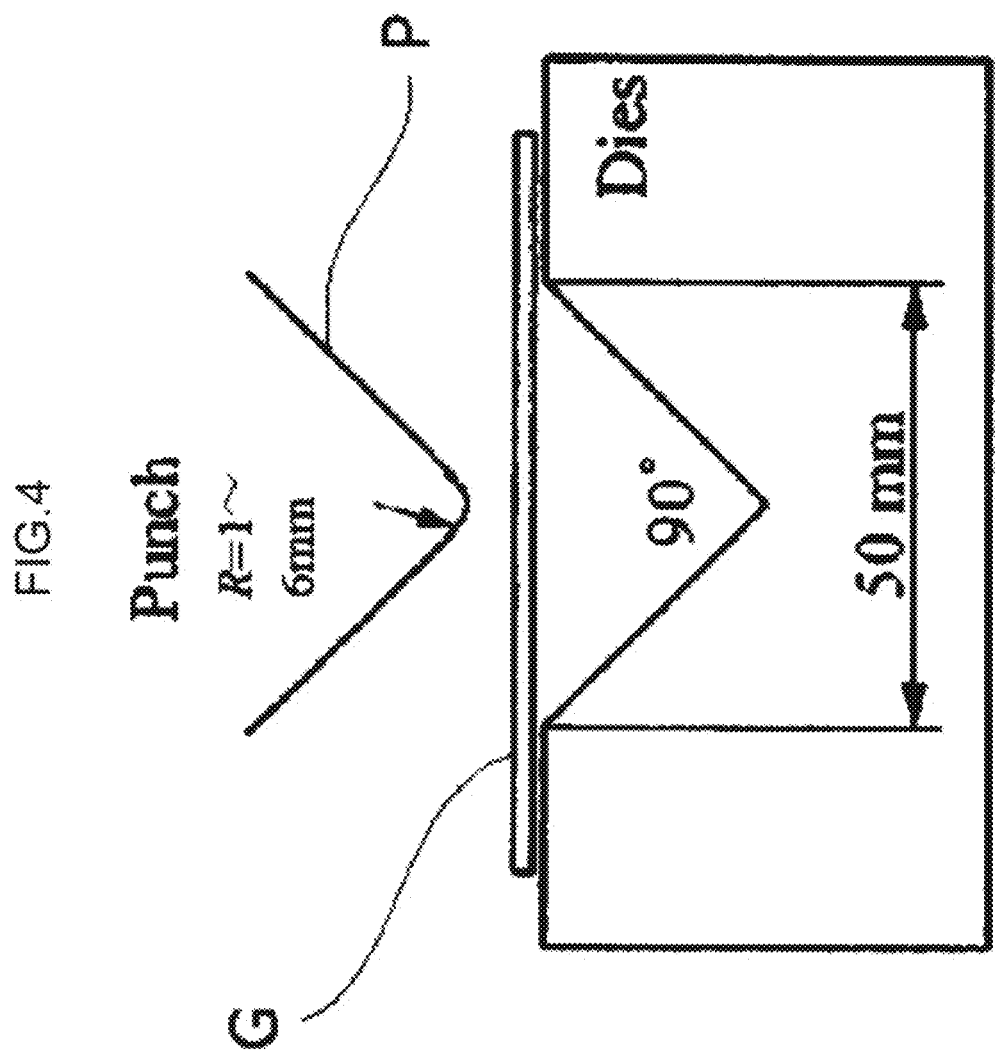
FIG. 4 is a diagram for explaining V-bend testing at an open angle of 90°.

The first risk ratio, which has the bending-surface limit stress as a criterion, is a method that evaluates fracture modes often seen in V-bend testing at an open angle of 90°, as illustrated in FIG. 4, and is known as a method for evaluating bending properties of high strength steel sheet. Bending tests for evaluating the first risk ratio employ a rectangular test piece G, cut out from a specimen steel sheet such that the length direction of the rectangular test piece G is a direction orthogonal to a compression/expansion direction. A length direction central portion of the rectangular test piece G is pressed into V-shaped die having an open angle of 90° by plural punches P that have a specific radius at their leading ends (for example, from 0.5 mm to 6.0 mm). The smallest bending radius is determined to be the smallest punch leading end radius out of punch leading end radii that do not generate visibly distinguishable fine cracks on the surface of the rectangular test piece G pressed into the die.

The bending properties of the high strength steel sheet are known to not correlate with either the total elongation or the n value, but to correspond well to a composition homogeneity index (see Kazumasa Yamazaki et al., Journal of the JSTP, 36-416 (1995), 973). Namely, in composite composition steel sheets having a non-homogeneous composition, it is thought that hard portions act as the origin of splitting due to strain concentrations arising due to hard portions preventing propagation of strain and due to the deformability of the hard portions themselves being low. However, it is known that excellent bending properties are known to be exhibited as long as composition is homogeneous, even in steel sheets substantially configured by a martensite phase having low deformability. In an exemplary embodiment of the present invention, in order to evaluate occurrence of cracks at the surface caused by non-homogeneous composition, the inherent bending-surface limit strain (also referred to as the bend outside limit strain) of the material was observed, and a bending-surface limit stress that is the bending-surface limit strain converted into stress is employed as a fracture determination criterion.

Bending-surface limit stresses are acquired for individual steel materials by bending tests such as the V-bend testing described above, and simulation that emulates such bending tests. Note that the bending test is not limited to V-bend testing at an open angle of 90°, and other testing methods may be employed, such as a 180° bend testing or measuring the smallest bend radius in an L-bend when steel is bent into an L shape using a punch and die.

Bending-surface limit stress can be found by simulation using a finite element method that models the smallest bending radius punch obtained from bending testing. A finite element method preferably uses code for a static implicit method formulated by plane strain elements, and simulates small enough element size to be capable of representing concentration of localized necking at the surface. However, a finite element method may also be one that uses shell elements formulated in a planar stress state in which there are five or more numeric integration points in the sheet thickness direction and the elements are divided at a size of approximately the sheet thickness.

Moreover, the fracture limit smallest bend radius can be found by bend testing using a V-type punch, and a bending-surface limit strain $\epsilon^0_\theta$ can be found from a sheet thickness $t_0$, a bend inside radius $r_i$, a bend outside radius $r_o$, and a bend neutral plane radius $R_n$.

The bending-surface limit strain $\epsilon^0_\theta$ can be found by calculation so as to satisfy:

$$\varepsilon^o_\theta = \ln((t + r_i)/R_n) \quad [1]$$

$$R_n = \frac{1}{2t_0}(r_o^2 - r_i^2) \quad [2]$$

$$t = \sqrt{2}\,R_n\left[\left\{1 + \left(\frac{t_0}{R_n}\right)^2\right\}^{1/2} - 1\right]^{1/2} \quad [3]$$

Other than simulation and calculation, the surface fracture limit strain can be found, after bending, from lines of a grid that was pre-transferred onto the material before deformation. For example, the bending-surface limit strain $\epsilon^0_\theta$ can be found by $$\varepsilon^o_\theta = \ln\left(1 + \frac{L - L_0}{L}\right) \quad [4]$$

wherein the grid separation before deformation is $L_0$, and the separation after bending is $L$.

Next, a static strain rate is assumed, and an equivalent stress—equivalent strain relationship equation obtained from uniaxial tensile testing is used to convert the above found bending-surface limit strain $\epsilon^0_\theta$ into a bending-surface limit stress $\sigma_1^{cr}$. Moreover, the major strain $\epsilon_1$ of the surface plane corresponding to the bend outside is calculated from surface plane strain tensors for each of the finite elements described in a local coordinate system, and the major strain $\epsilon_1$ of the surface plane is converted into a bending-surface major stress $\sigma_1$. As represented by the equation below, the ratio of the bending-surface major stress $\sigma_1$ to the bending-surface limit stress $\sigma_1^{cr}$ is a first risk ratio F1.

$$\text{First risk ratio: } F1 = \frac{\sigma_1}{\sigma_1^{cr}} \quad [5]$$

Second Risk Ratio

Figure 5:
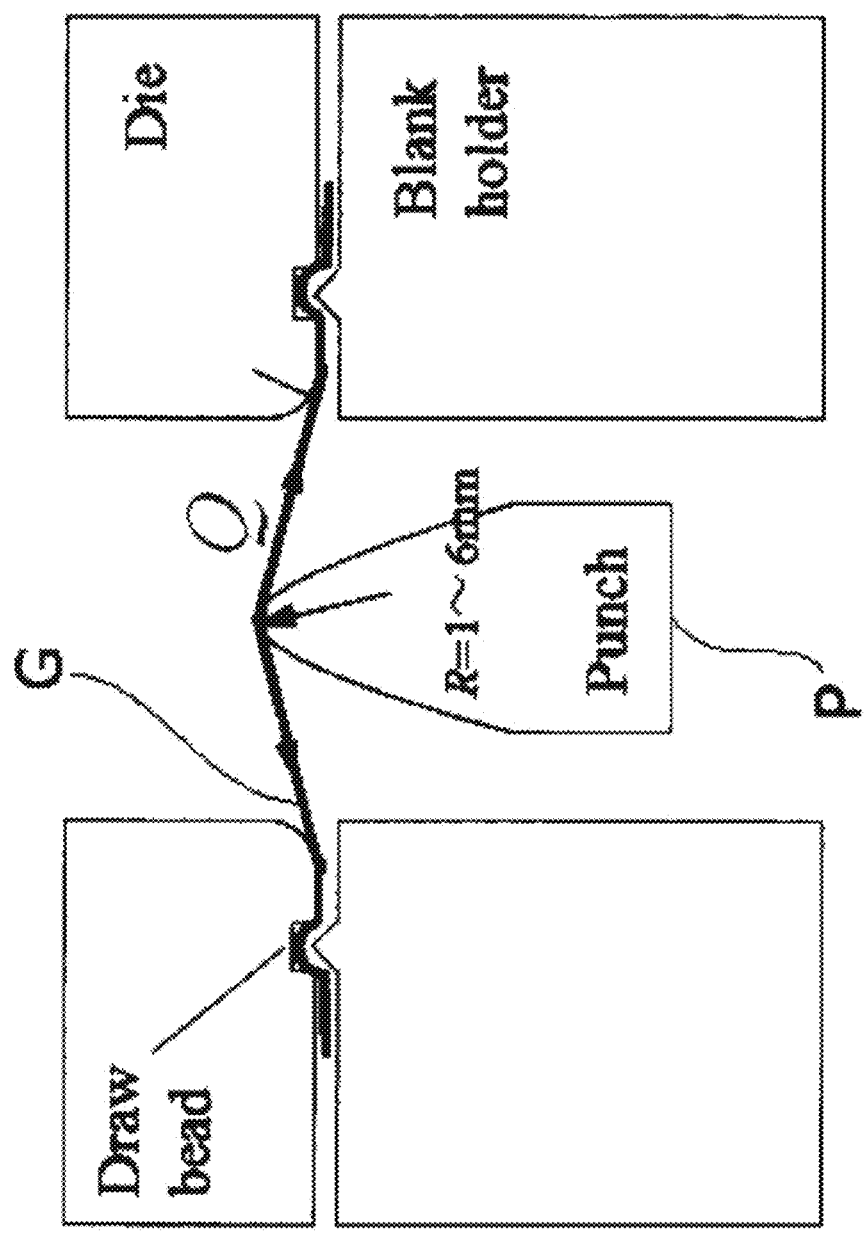
FIG. 5 is a diagram for explaining stretch bending testing.
Figure 6:
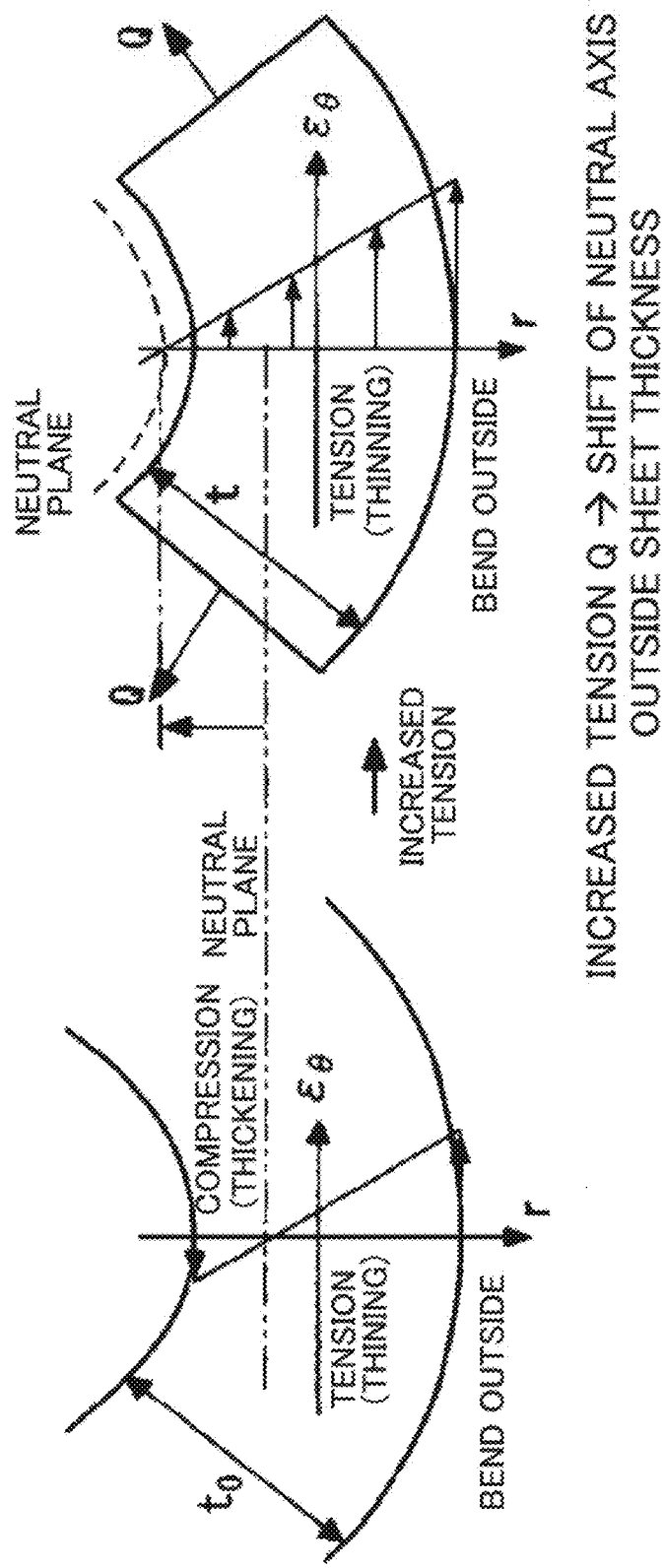
FIG. 6 is a diagram for explaining differences between strain states of pure bending and stretch bending.

The fracture mechanism in a stretch bending test may be thought of as follows. Namely, as illustrated in FIG. 6, in the case of a pure bend in which only a bending moment acts, circumferential strain decreases and radial direction compression strain increases in the material from the bend outside toward the bend inside. In contrast, as illustrated in FIG. 5 and FIG. 6, in the case of stretch bending in which tensile force and a bending moment act simultaneously, the neutral plane is shifted toward the bend inside by the tensile force, causing a reduction in sheet thickness and inducing plastic strain in the direction of tension. After inducing plastic strain in the tension direction, if the tensile force is further increased then the work hardening ratio of the material decreases due to tensile deformation. In cases in which the work hardening ratio decreases, localization of deformation progresses since sufficient hardness is not obtained to balance the reduction in sheet thickness, leading to fracture after localized necking has arisen. Moreover, even while the same tensile force is being applied, the neutral plane shifts further toward the bend inside as the bend radius decreases. Localization of strain becomes more liable to occur due to the neutral plane shifting even further toward the bend inside, leading to fracture occurring after pronounced sheet thickness reduction (localized necking) has been observed in the bend leading end portion.

Explanation is first given regarding bending plastic instability under tensile force in order to explain the process leading up to fracture. Plastic instability conditions under which localized necking arises may be considered in bending deformation under plane strain deformation in cases in which a tensile force per unit width Q and a bending moment M act. Herein, assuming (1) deformation of the bend portion is considered to be uniform bending and shear deformation is not considered, (2) as plane strain deformation, and (3) according to the constant volume law, (4) a von Mises yield function is employed so as to enable (5) the relationship between equivalent stress and equivalent plastic strain to be represented as $\sigma_{eq}=c\epsilon^n_{eq}$ when approximated by an n-power hardening law. Given these conditions, a peripheral direction stress distribution $\sigma_\theta$ and a radial direction stress distribution $\sigma_r$ are respectively given by the following equations:

$$\sigma_r = c\left(\frac{2}{\sqrt{3}}\right)^{n+1}\left[\pm\frac{1}{n+1}\left(\left|\ln\frac{r}{R_n}\right|\right)^{n+1} + \frac{1}{n+1}\left(\ln\frac{R_n}{r_i}\right)^{n+1}\right] - p \quad [6]$$

$$\sigma_\theta = \sigma_r + c\left(\frac{2}{\sqrt{3}}\right)^{n+1}\left(\left|\ln\frac{r}{R_n}\right|\right)^n \quad [7]$$

wherein, the radial direction coordinate of the bend portion is r, the bend inside radial coordinate in this case is $r_i$, the radial coordinate of the bend outside is $r_o$, and the radial coordinate of the neutral plane is $R_n$. Moreover, c and n are characteristic parameters of the material, p is the radial direction stress, $\sigma_{ri}=-p=Q/r_i$, at bend radius $r_i$. From these equations, the tensile force q is given by the following equation:

$$q = \frac{Q}{t_0} = \frac{1}{t_0}\int_{r_i}^{r_o}\sigma_\theta dr = c\left(\frac{2}{\sqrt{3}}\right)^{n+1}\frac{r_i}{t_0}\frac{1}{n+1}\left[\left|\ln\frac{r_o}{R_n}\right| \pm \left(\ln\frac{R_n}{r_i}\right)^{n+1}\right] \quad [8]$$

Moreover, for a known q, material sheet thickness $t_0$, and bend inside radius $r_i$, the tensile strain $\epsilon_1=-\ln(t/t_0)$ corresponding to the post-bending deformation sheet thickness $t=r_o-r_i$, and the acting tensile force q can be found by finding an $r_o$ and an $R_n$ that satisfy Equation (3) and a conditional equation for the constant volume law:

$$t_0 = \frac{r_o^2 - r_i^2}{2R_n} \quad [9]$$

Moreover, the plastic instability of plane strain stretch bending can be found by the maximum load condition equation:

$$\frac{dq}{d\epsilon_1} = 0 \quad [10]$$

The tensile force in this case $q=q_{cr}$ can also be employed as a fracture determination criterion. Moreover, a curvature $(1/\rho)$ that satisfies the instability condition equation of bending moment can also be employed as a fracture determination criterion.

$$\frac{dM}{d(1/\rho)} = 0 \quad [11]$$

As described above, the tensile force $q_{cr}$ and the fracture limit curvature $(1/\rho)$ can be employed as threshold values for fracture determination. However, considering that the bending surface major stress $\sigma_1^{cr}$ that is the threshold value of the first risk ratio is a dimension of stress, fracture determination can be performed with greater precision when the threshold value of the second risk ratio to be compared to the first risk ratio is also considered as a dimension of stress.

A bending fracture limit stress $\sigma_{OB}^{cr}$ that is criterion for computing the second risk ratio is found in light of the above.

(2)-1

First, the fracture limit stress is found for respective amounts of bending $R/t_0$ from a theoretical solution to the relationship between stress and strain of a plane strain stretch bending. A true stress $\sigma_1$ in the plane strain tension direction of the bend surface is given by the following equation. Note that R represents the bending radius of the sheet thickness center line.

$$\sigma_1 = q\frac{t_0}{t} \quad [12]$$

Moreover, a bending fracture limit stress $\sigma_{cr}$ corresponding to the bend amount $R/t_0$ is calculated from the work hardening ratio and from the equation below that gives a condition for necking occurrence for plane strain tension.

$$\frac{d\sigma_1}{d\epsilon_1} = \sigma_1 \quad [13]$$

Figure 7:
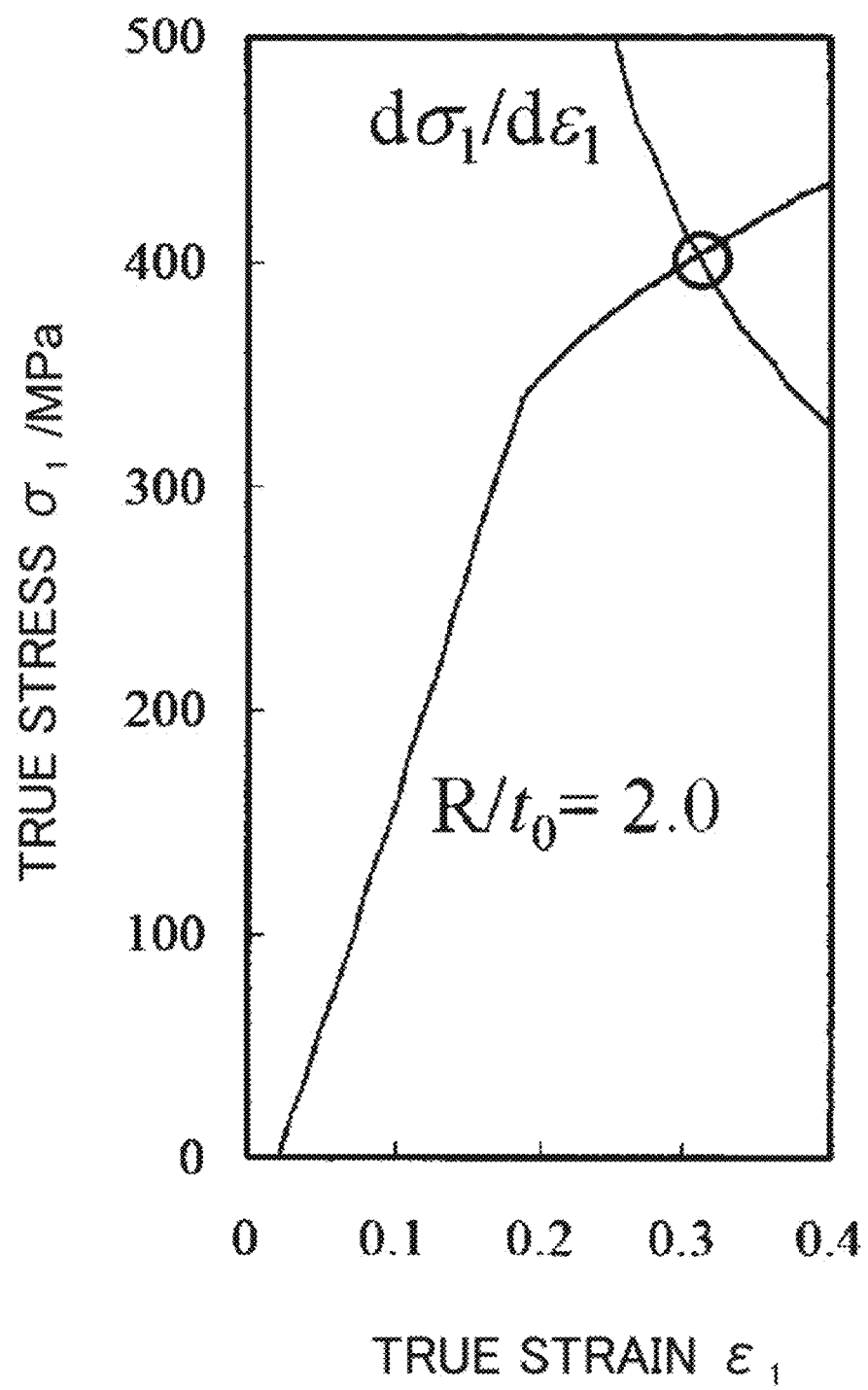
FIG. 7 is a diagram illustrating a relationship between true stress and true strain in cases in which $R/t_0$ is 2.0.
Figure 8:
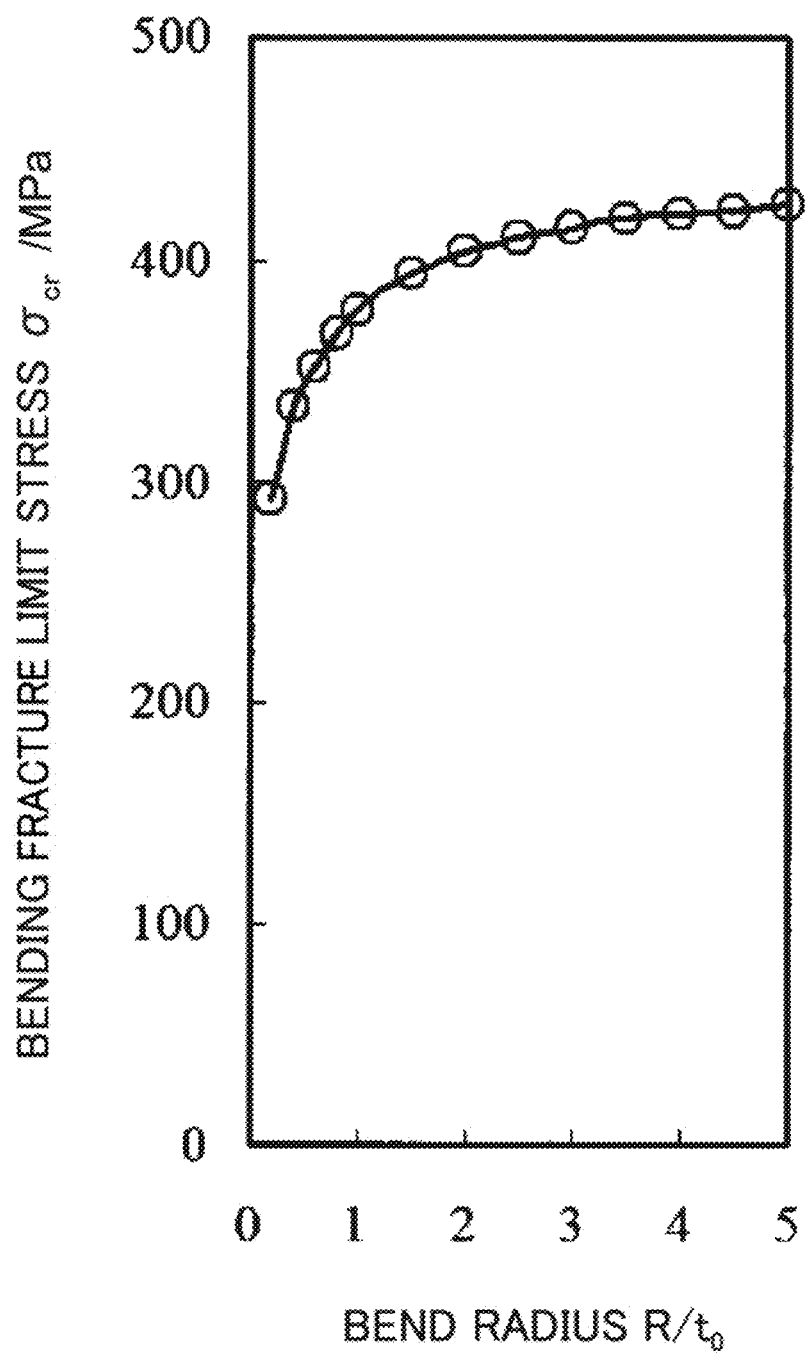
FIG. 8 is a diagram illustrating a bending fracture limit stress $\sigma_{CT}$ for each bend amount $R/t_0$.

FIG. 7 illustrates a relationship between the true stress and the true strain in cases in which $R/t_0$ is 2.0. A $\sigma_1$ satisfying the above necking occurrence condition $(d\sigma_1/d\epsilon_1=\sigma_1)$, namely, a bending fracture limit stress $\sigma_{cr}$, is calculated as shown in this graph. As illustrated in FIG. 8, the bending fracture limit stress $\sigma_{cr}$ is calculated for respective amounts of bending $R/t_0$.

(2)-2

Next, a criterion in space of stresses is found under an assumption of a static strain rate, from the work hardening characteristics obtained by uniaxial tensile tests on the material.

First, the work hardening characteristics from uniaxial tensile testing are expressed by the following equation, and the fracture limit stress in space of stresses is found from this equation.

$$\sigma_{eq} = f(\epsilon_{eq}) \quad [14]$$

As an example, when $\sigma_{eq}$ is:

$$\sigma_{eq} = K(\epsilon_0 + \epsilon_{eq})^{n*} \quad [15]$$

the following equations can be obtained with fracture limit stress employing a principal stress ratio ($\alpha = \sigma_2/\sigma_1$) and a material strain-hardening exponent $n = n^* - \epsilon_0$.

$$\sigma_1 = \frac{c}{\sqrt{1+\alpha^2-\alpha}} \left[ \frac{4n(1-\alpha+\alpha^2)^{3/2}}{4-3\alpha-3\alpha^2+4\alpha^3} \right]^n \quad [16]$$

$$\sigma_2 = \alpha \sigma_1 \quad [17]$$

Figure 9:
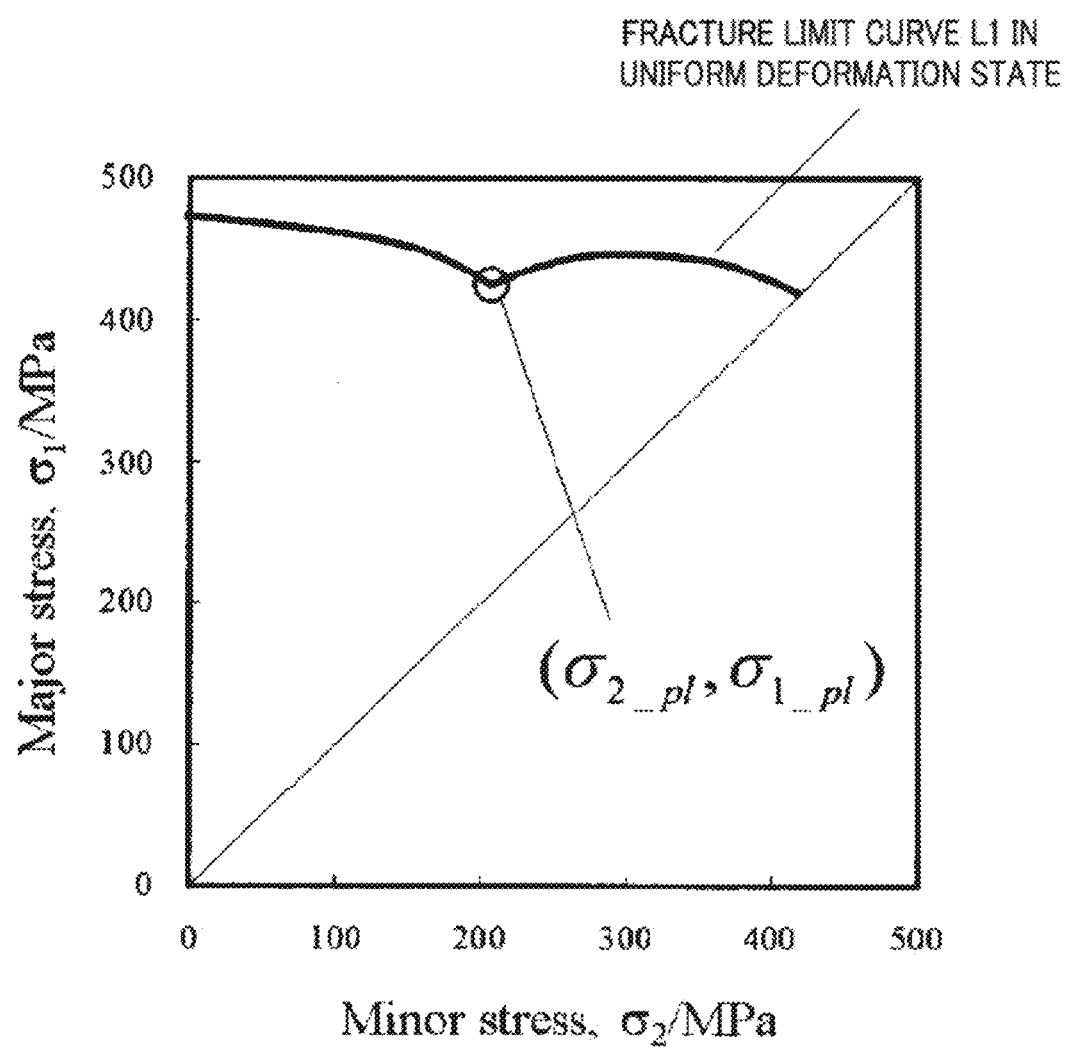
FIG. 9 is a diagram illustrating a fracture limit curve represented in space of stresses.

FIG. 9 illustrates an FLD based on uniaxial tensile tests. As indicated by this graph, a fracture limit curve L1 can be obtained by changing the constant $\alpha$ in the equation within a range of from 0 to 1 (by changing the principal stress ratio).

Although description has been given regarding a method to find the fracture limit curve L1 represented in space of stresses from the work hardening characteristics obtained from uniaxial tensile testing on the material, the fracture limit curve L1 can be found by converting from the FLD in space of strains actually measured, as described below, into the space of stresses. The FLD in space of strains is a diagram indicating, for respective minor strains $\epsilon_{22}$, a major strain $\epsilon_{11}$ to achieve the fracture limit, and the sheet thickness strain $\epsilon_{33}$ can be found by these major strains $\epsilon_{11}$ and the constant volume law, $\epsilon_{33} = -(\epsilon_{11} + \epsilon_{22})$. Herein, equivalent plastic strain can be represented by employing the von Mises yield function on the yield surface curve.

$$\varepsilon_{eq} = \int d\varepsilon_{eq} = \int \sqrt{\frac{2}{3} d\varepsilon_{ij} d\varepsilon_{ij}} \quad [18]$$

wherein $\epsilon_{eq}$ represents the equivalent plastic strain, $d\epsilon_{eq}$ represents an equivalent plastic strain rate, and $d\epsilon_{ij}$ represents a plastic strain rate tensor.

A stress component $\sigma_{ij}$ is then represented by the following equation assuming equivalent hardnening and the perpendicular axis theorem for the yield surface curve, and planar stress. Note that $\sigma_{ij}$ is the Kronecker delta.

$$\sigma_{ij} = \frac{2}{3} \frac{c\varepsilon_{eq}^n}{d\varepsilon_{eq}} (d\varepsilon_{ij} - d\varepsilon_{33}\delta_{ij}) \quad [19]$$

The fracture limit curve L1 represented in space of stresses can be calculated according to the above. Moreover, the fracture limit curve L1 can also be found by converting a theoretically derived FLD in space of strains into space of stresses. For example, in cases in which the work hardening law of the material is approximated by to an n-power law then:

$$\varepsilon_{11} = \frac{n}{1+\rho} \left( \rho = \frac{d\varepsilon_{22}}{d\varepsilon_{11}} \leq 0 \right) \quad [20]$$

$$\varepsilon_{11} = \frac{2n(\rho^2 + \rho + 1)}{(\rho+1)(2\rho^2 - \rho + 2)} (\rho > 0) \quad [21]$$

$$\varepsilon_{22} = \rho\varepsilon_{11} \quad [22]$$

The FLD in the space of strains can be obtained by changing the constant $\rho$ within the range of from $-0.5$ to $1$ in equations 20 to 22 above, and the fracture limit curve L1 can be found for a first deformation mode in the space of stresses by converting this FLD into the space of stresses by the method described above. Note that $\rho$ represents a plastic strain rate ratio.

(2)-3

Figure 10:
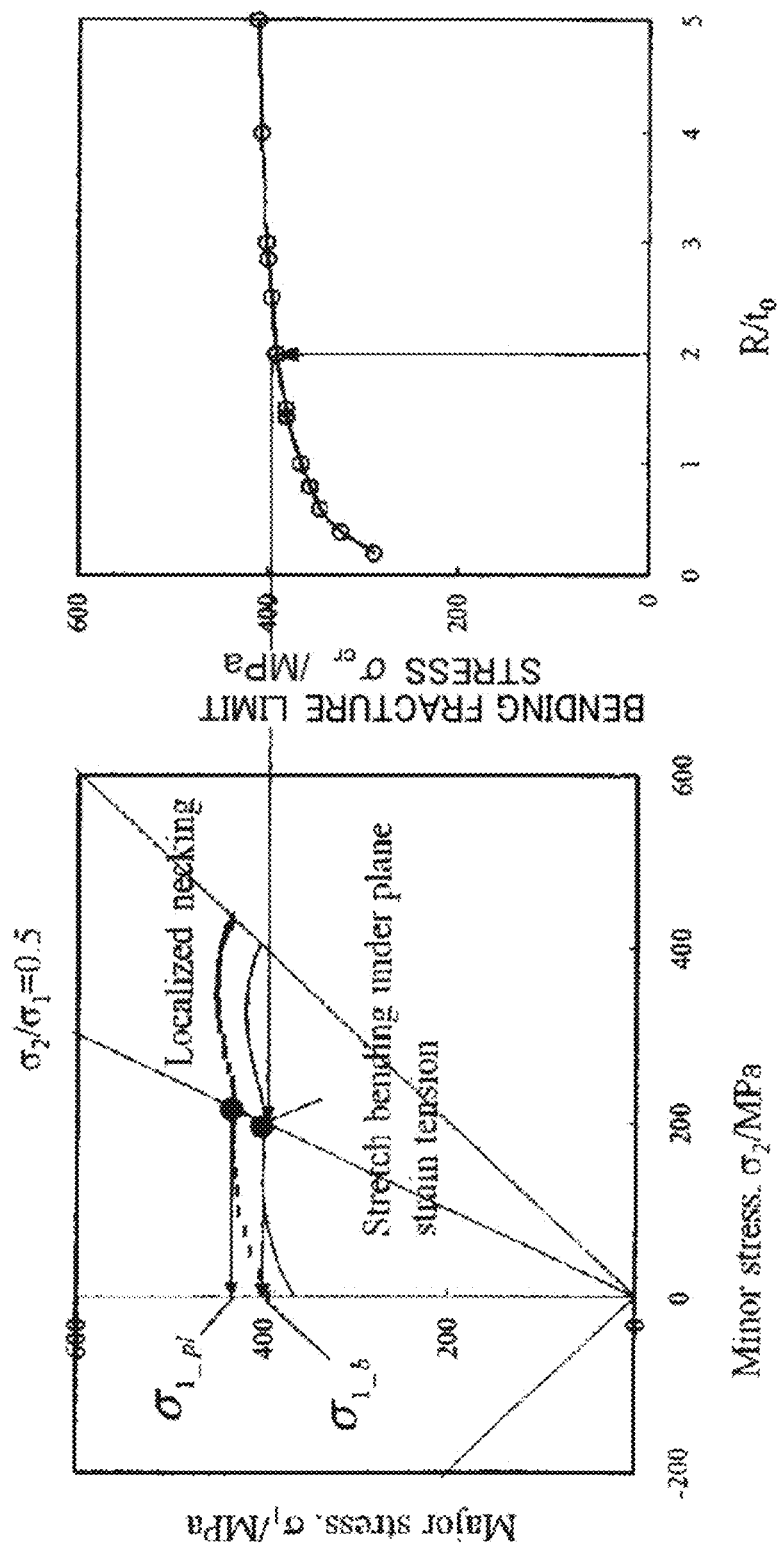
FIG. 10 is a diagram for explaining a process of finding a fracture limit curve corresponding to a bend amount $R/t_0$ from a fracture limit curve in a uniform deformation state represent in space of stresses.

Next, under plane strain deformation, a stretch bending fracture limit curve L2 under plane strain deformation is found by offsetting the criterion found in (2)-2 above (the fracture limit curve L1). More specifically, as illustrated in FIG. 10, the fracture limit curve L2 can be obtained by offsetting the fracture limit curve L1 (the formation limit diagram) obtained in (2)-2 so as to correspond to fracture limit stresses $\sigma_{cr}$ for the respective bend amounts $R/t_0$ found in (2)-1 above.

Bringing the above all together, a ratio $\gamma$ of the bending fracture limit stress $\sigma_{cr}$ corresponding to the bend amount $R/t_0$ of elements subject to determination in the metal sheet, to the plane strain fracture limit stress $\sigma_{1\_pt}$ in a uniform deformation state, is determined and a fracture limit curve L2 corresponding to the bending amount $R/t_0$ is calculated by multiplying the stress components of the fracture limit curve L1 by the ratio $\gamma$.

$$\gamma = \frac{\sigma_{1\_b}}{\sigma_{1\_p1}} \quad [23]$$

Figure 11:
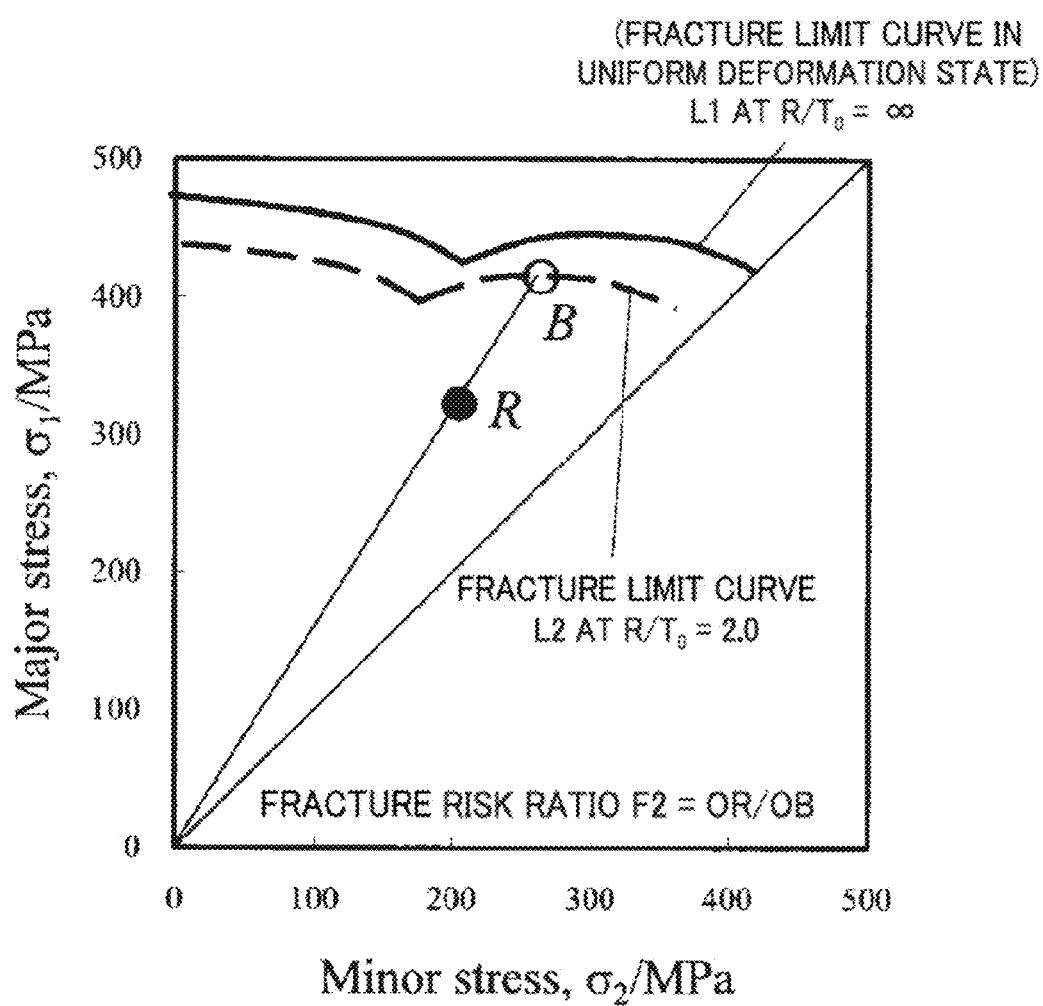
FIG. 11 is a diagram for explaining a process of finding a second risk ratio $F2=\sigma_{OR}/\sigma_{OB}^{cr}$.

In the fracture limit curve L2 of the stretch bending illustrated in FIG. 11, the point indicated by the reference symbol R is a stress state found by converting a plastic strain tensor into a stress tensor under the assumption of a static strain rate for all of the elements subject to evaluation. The reference symbol B indicates the point of intersection between a line passing through the origin and R, and the fracture limit curve L2, and the point indicated by the reference symbol B is the bending fracture limit stress state of the elements subject to evaluation. The ratio of these stresses $\sigma_{OR}$ to fracture limit stress $\sigma_{OB}^{cr}$ is the second risk ratio F2, serving as a risk ratio.

$$\text{Second risk ratio: } F2 = \frac{\sigma_{OR}}{\sigma_{OB}^{cr}} \quad [24]$$

Metal Sheet Bending Fracture Determination Method and Program for the Same

Explanation next follows regarding a method for determining bending fracture of a metal sheet in an exemplary embodiment of the present invention.

Figure 12A:
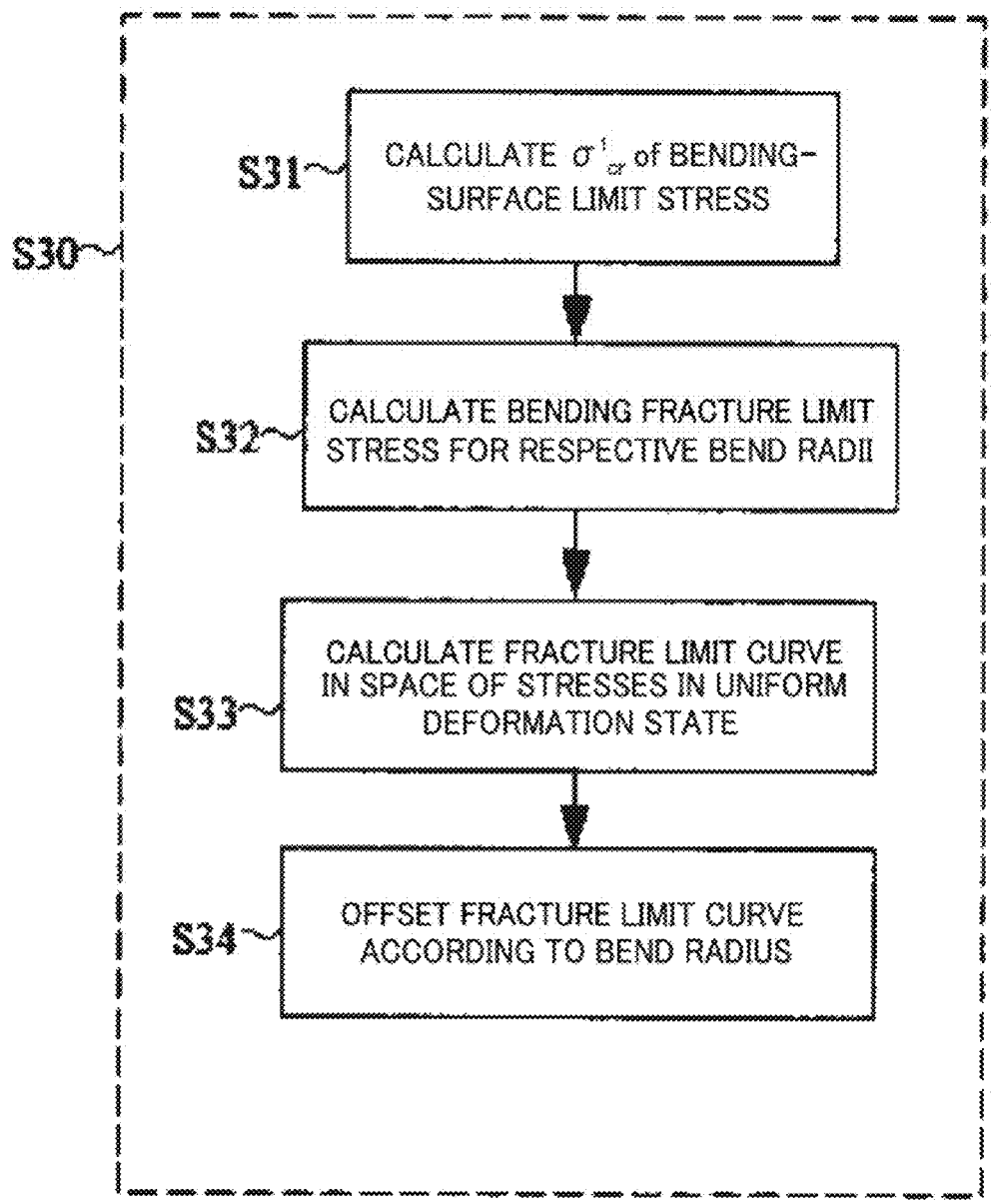
FIG. 12A is a diagram illustrating part of a flowchart of an algorithm executed by a fracture determination device.
Figure 12B:
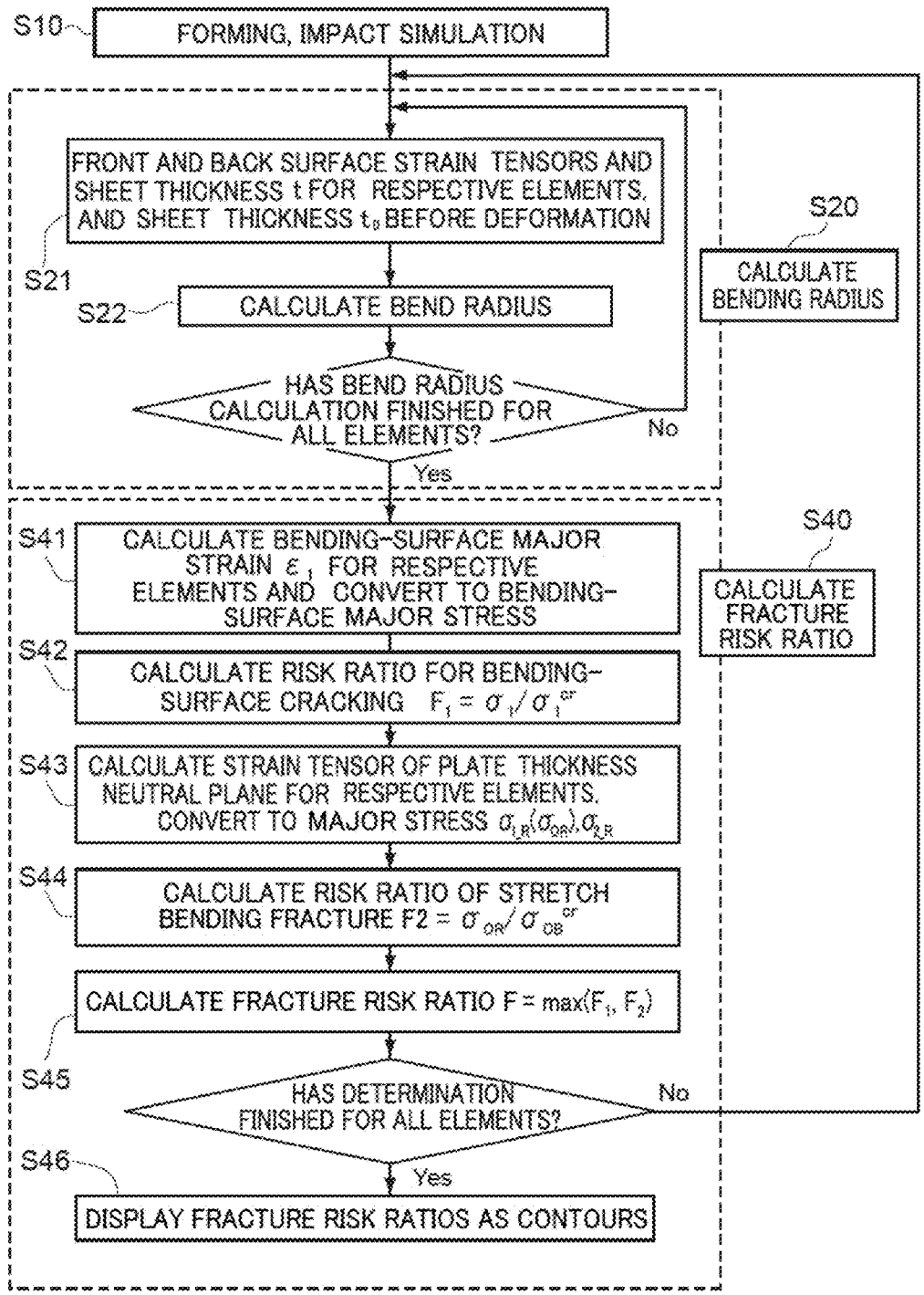
FIG. 12B is a diagram illustrating another part of a flowchart of an algorithm executed by a fracture determination device.

FIG. 12A and FIG. 12B are diagrams illustrating flowcharts of algorithms executed by a fracture determination device according to the exemplary embodiment of the present invention. The fracture determination device employs a computer program that includes the algorithms illustrated in FIG. 12A and FIG. 12B.

The program includes an extraction means 10, a bend radius calculation means 20, a fracture determination criterion calculation means 30, and a determination means 40, and includes functionality to cause a computer to execute each of these means. The extraction means 10 executes processing of step S10 to obtain a sheet thickness and strain tensors for the front and back surfaces of each element mid-deformation obtained by forming analysis or crash analysis. The bend radius calculation means 20 executes processing of step S20 to calculate the bend radius for each element obtained by forming analysis or crash analysis. The fracture determination criterion calculation means 30 executes the processing of step S30 to calculate a fracture determination criterion based on input material parameters. The determination means 40 executes processing of step S40 to calculate, for each element, the first risk ratio F1, which is a risk ratio for bending surface cracks, and the second risk ratio F2, which is a risk ratio for stretch bending fracture, and to perform fracture determination for the fracture mechanism having the higher fracture risk ratio out of the first risk ratio and the second risk ratio.

First, at step S10, the extraction means 10 calculates strain tensors for the front and back surfaces and sheet thickness t for each element in a deformation process using a numerical analysis program such as a finite element method, and inputs the calculation result into a user subroutine or an external program that determines bending fracture.

Next, at step S21, for each element subject to determination, the bend radius calculation means 20 calculates, for each element described in a local coordinate system, the curvature for each component, and in-plane maximum curvature and minimum curvature, from the strain tensors and the sheet thickness of the elements during deformation. Next, at step S22, the bend radius calculation means 20 calculates the minimum bending radius R of a three dimensional curved surface.

Next, at step S31, the fracture determination criterion calculation means 30 acquires the characteristic bending-surface limit strain $\epsilon^0_\theta$ of the material as obtained from the minimum bend radii for respective steels obtained from experiment, such as V-bend testing at 90° open angle or L-bend testing. Then, the bending-surface limit strain $\epsilon_0^\theta$ is converted into the bending-surface limit stress $\sigma_1^{cr}$ under the assumption of a static strain rate. Moreover, at step S31, the fracture determination criterion calculation means 30 acquires the equation $\sigma_{eq}=f(\epsilon_{eq})$ for the relationship between the equivalent stress $\sigma_{eq}$ and the equivalent plastic strain $\epsilon_{eq}$ of the material, and acquires $f(\epsilon_{eq})$, which is an indicator of plastic anisotropy. Although a high-order polynomial equation or another equation form of $\epsilon_{eq}$ may be employed as the function of work hardening $f(\epsilon_{eq})$, n-power hardening law or Swift's equation, which are highly precise approximations that are often used in forming simulation and crash simulation, are preferably employed therefor.

Next, at step S32, the fracture determination criterion calculation means 30 calculates the bending fracture limit stress $\sigma_{cr}$ for each bend amount $R/t_0$ from Equation (12) and Equation (13). Next, at step S33, criteria are found in space of stresses, under the assumption of static strain rate, from work hardening characteristics obtained from uniaxial tension experiments on the material. Namely, the fracture limit stress $\sigma_{l\_p1}$ and the fracture limit curve L1 illustrated in FIG. 9 are found from Equation (14) to Equation (17). Then, at step S34, the ratio γ (see Equation (23)) corresponding to the bend amount $R/t_0$ of the elements subject to determination is determined, and a fracture limit stress $\sigma_{1\_b}$ under plane strain stress is determined. Moreover, the ratio γ of the bending fracture limit stress $\sigma_{cr}$ corresponding to the bend amount $R/t_0$ of the elements subject to determination of a metal sheet, to the plane strain fracture limit stress $\sigma_{l\_p1}$ in a uniform deformation state of a metal sheet, is determined and the fracture limit curve L2 is calculated corresponding to the bend amount $R/t_0$ by multiplying the stress component of the fracture limit curve L1 by the ratio γ.

Next, at steps S41 to S46, the determination means 40 calculates the fracture risk ratio for all of the elements subject to determination, and displays values of the fracture risk ratio F as contours by post processing.

First, at step S41, the determination means 40 calculates the major strain ε1 of the surface plane corresponding to the bend outside from front and back surface strain tensors for each of the finite elements described in the local coordinate system, and converts the major strain $\epsilon_1$ of the surface plane into bending-surface major stresses $\sigma_1$. Next, at step S42, the determination means 40 calculates the first risk ratio $F=\sigma_1/\sigma_1^{cr}$ which is the risk ratio for bending-surface cracking, from the bending-surface limit stress $\sigma_1^{cr}$ acquired for each of the steels at step S31 and the magnitudes of bending-surface major stress $\sigma_1$ of each of the elements.

Next, at step S43, the determination means 40 calculates the stress $\sigma_{OR}$ under plane strain stress of the finite elements, and calculates the fracture limit stress $\sigma_{OB}^{cr}$ corresponding to the stress ratio of the finite elements from the fracture limit stress $\sigma_{l\_b}$ calculated at step S34. Next, at step S44, the determination means 40 calculates the second risk ratio $F2=\sigma_{OR}/\sigma_{OB}^{cr}$, which is a risk ratio for stretch bending fracture, from the stress $\sigma_{OR}$ calculated at step S34 and the magnitude of the fracture limit stress $\sigma_{OB}^{cr}$.

Next, at step S45, the determination means 40 determines the risk ratio for bending fracture as the larger out of the first risk ratio F1 calculated at step S42 and the second risk ratio F2 calculated at step S44. Then, at step S46, the determination means 40 displays index values of the fracture risk ratio F as contours by post processing.

The bend portion fracture determination method of the present exemplary embodiment thus enables determination of a fracture risk ratio for respective bending fractures occurring by two different mechanisms: a fracture mode in which cracking occurs on the bend outside surface without the appearance of obvious localized necking, and a fracture mode in which fracture occurs after observing a pronounced sheet thickness reduction (localized necking) in the bend leading end portion even though cracking does not occur at the bend outside. This enables quantitative determination of risk that fracture is liable to occur or that fracture has occurred by either fracture mechanism, for complex phenomena such as deformation during press forming and crashes. As a result, a structure, material, or the like can be selected at the design stage so as preemptively prevent fracture of steel sheet, enabling digital development of vehicle bodies that are excellent in terms of low weight and crash safety.

Each functionality configuring the determination device according to the present exemplary embodiment, and each step configuring the determination method according to the present exemplary embodiment explained with reference to FIG. 12A and FIG. 12B, can be implemented by operations based on a program stored in RAM, ROM, or the like of a computer. A program that executes each step configuring the determination processing according to the present exemplary embodiment, and a computer readable storage medium storing the program, are included in exemplary embodiments of the present invention.

More specifically, the program for executing each step configuring the determination method according to the present exemplary embodiment is provided to a computer by recording on a recording medium such as a CD-ROM or the like, or via various transmission media. A recording medium that records a program for executing each step configuring the determination method according to the present exemplary embodiment may be a flexible disk, a hard disk, magnetic tape, magneto-optical tape, a non-volatile memory card, or the like. A transmission medium of the program for executing each step configuring the determination method according to the present exemplary embodiment may employ a communications medium in a computer network to supply the program data by transmitting the program data on a carrier wave. The computer network is, for example, a LAN, a WAN such as the internet, or a wireless communications network, and the communication medium is, for example, a wired circuit such as an optical fiber or wireless circuit.

Programs included in the present exemplary embodiment are not limited to those that implement the above functions by executing a supplied program on a computer. For example, the present exemplary embodiment includes a program in which the functionality of each step configuring the determination method according to the present exemplary embodiment is implemented in cooperation with an operating system (OS), or other application software or the like, operating on a computer. The present exemplary embodiment also includes a program employed in cases in which all or part of the processing of the supplied program is implemented by execution by a functionality enhancing board or a functionality enhancing unit of a computer.

Figure 13:
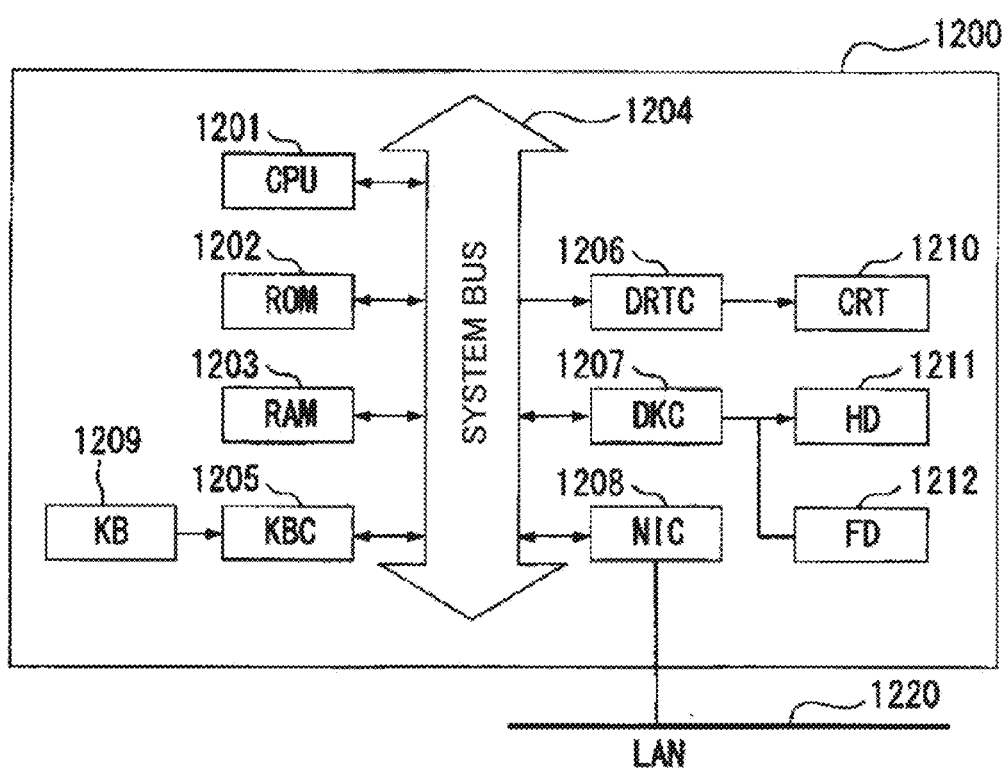
FIG. 13 is a schematic diagram illustrating an internal configuration of a personal user terminal device.

FIG. 13 is a schematic diagram illustrating an internal configuration of a personal user terminal device.

A personal computer (PC) 1200 includes a CPU 1201. The PC 1200 executes device control software stored in ROM 1202 or on a hard disk (HD) 1211, or supplied using a flexible disk drive (FD) 1212. The PC 1200 performs integrated control of each device connected to a system bus 1204. A strength determination system is implemented by a program stored in the CPU 1201 and the ROM 1202, or on the hard disk (HD) 1211, of the PC 1200. RAM 1203 functions as primary memory, a working area, and the like, for the CPU 1201. A keyboard controller (KBC) 1205 controls instruction input from a keyboard (KB) 1209, other devices, not illustrated in the drawings, and the like. A CRT controller (CRTC) 1206 controls display by a CRT display (CRT) 1210. A disk controller (DKC) 1207 controls access to the hard disk (HD) 1211 and the flexible disk drive (FD) 1212 storing a boot program, plural applications, editing files, user files, network management programs, and the like. The boot program is a startup program that initiates hardware of a personal computer and execution of software. A NIC 1208 executes two-way data communications with a networked printer, other network devices, and other PCs.

Note that although explanation has been given regarding an example in which the larger out of the first risk ratio F1 and the second risk ratio F2 is determined as the bending fracture risk ratio in the above metal sheet bending fracture determination method, the present invention is not limited thereto. For example, in cases in which there is no need to consider the fracture mode in which cracking occurs on the bend outside surface without the appearance of obvious localized necking (for example, cases in which the steel sheet has sufficient ductility), the bending fracture ratio may be a risk ratio corresponding to the second risk ratio F2 alone.

EXAMPLE

Explanation follows regarding an example of the present invention. Fracture determination according to the present exemplary embodiment was applied in three-point bending crash analysis of a frame having a hat shaped cross-section to investigate the validity of the above metal sheet bending fracture determination method.

Figure 14:
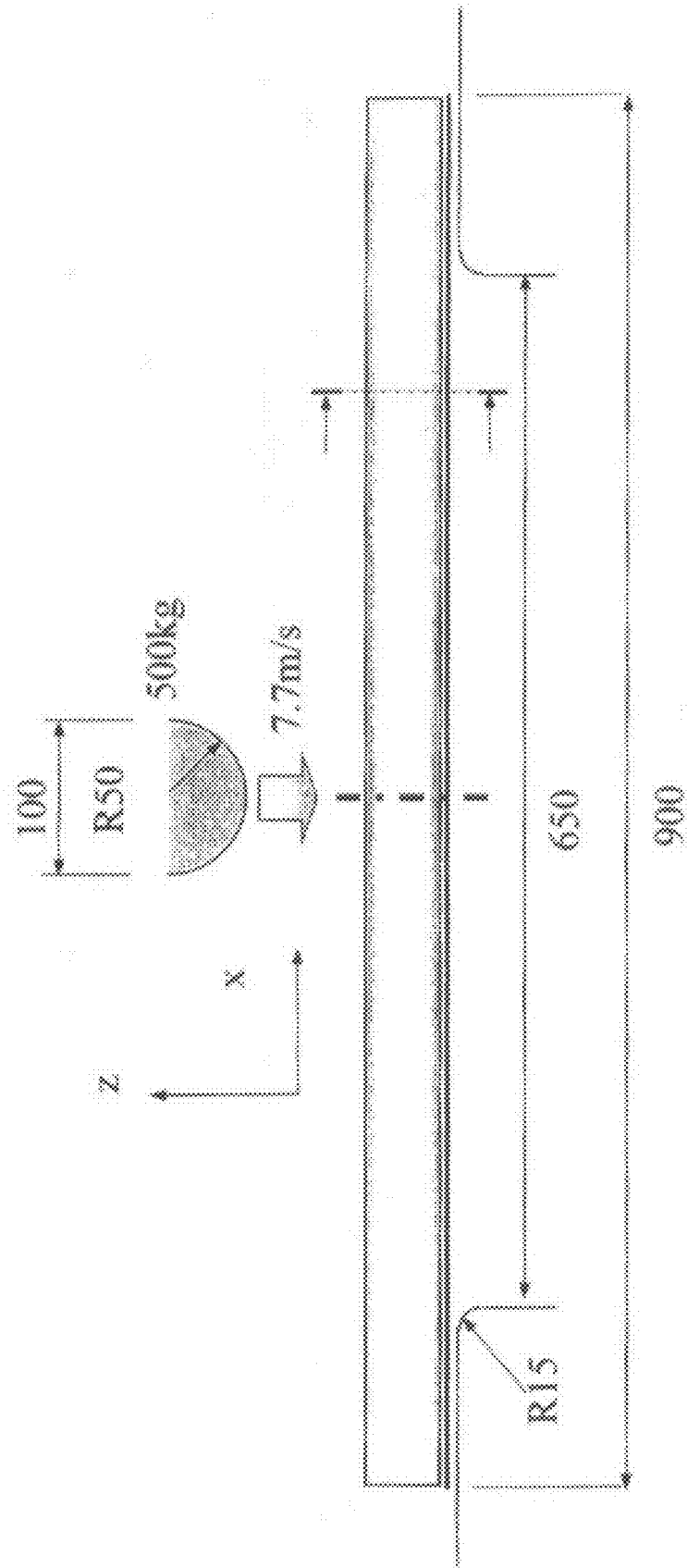
FIG. 14 is a diagram illustrating calculation conditions for a three-point crash analysis employed in examples of the present invention.

FIG. 14 is a diagram illustrating three-point bending drop test conditions and calculation conditions for crash analysis employed in the example of the present invention.

The frame serving as the subject was a hat shaped member, and was a member 900 mm in length having a cross-section closed by a closing plate. The sample material was high strength steel sheet having a sheet thickness of 1.8 mm, and the hat-shaped member and the closing plate were joined together by spot welding performed to flange portions at a 30 mm pitch. A 500 kg weight was caused to fall freely onto the sample body from a height of 3m so as to crash at an initial speed of 7.7 m/s. As a result, (1) the member was deformed along a loader from the start of crash until a maximum reaction force was observed, (2) subsequently, the reaction force began to decrease at a timing at which the wall surface was deformed toward the outside and a transition was made to a rupturing mode in the length direction, and (3) the reaction force monotonically decreased as deformation progressed. Then, when inspecting the sample body after testing, cracking was confirmed at a locally deformed portion bent into a V-shape.

FIG. 15 is a diagram illustrating fracture risk found using the present metal sheet bending fracture determination method for the three-point bending crash analysis employed in the example of the present invention, displaying isopleths as contours. FIG. 15 illustrates a result displaying fracture risk values (the value of the larger out of the first risk ratio F1 and the second risk ratio F2) as isopleths.

Determination was made that there was a higher risk of fracture the greater the fracture risk value in FIG. 15 was, and that the material fractured in cases in which the value of the larger of the first risk ratio F1 and the second risk ratio F2 reached 1.0. It is apparent that analysis showing a high risk of fracture at bend portions where cracking occurred in the drop test was excellently reproduced in the experiment.

Fracture risk values mid-deformation during a crash can accordingly be determined quantitatively by the present metal sheet bending fracture determination method enabling the investigation of structure and material selection to preemptively prevent fracture of sheet steel at the design stage, thereby enabling the digital development of vehicle bodies having excellent light weight and crash safety.

Description follows regarding preferable modes of the present invention.

A metal sheet bending fracture determination method according to a first aspect includes: calculating a bending fracture limit stress $\sigma_{cr}$ for each bend amount $R/t_0$ of a metal sheet; calculating a fracture limit curve L1 for a uniform deformation state in space of stresses under the assumption of static strain rate and calculating a fracture limit stress $\sigma_{l\_p1}$ under plane strain deformation, from work hardening characteristics obtained by uniaxial tensile testing of a material configuring the metal sheet; determining a ratio γ of the bending fracture limit stress $\sigma_{cr}$ corresponding to the bend amount $R/t_0$ of the elements subject to determination of the metal sheet, to the plane strain fracture limit stress $\sigma_{\perp p1}$ in the uniform deformation state, and calculating a fracture limit curve L2 corresponding to the bend amount $R/t_0$ by multiplying a stress component of the fracture limit curve L1 by the ratio $\gamma$; calculating a corresponding fracture limit stress $\sigma_{OR}^{cr}$ from the major stress $\sigma_{OB}$ of the element subject to determination and the fracture limit curve L2 corresponding to the bend amount $R/t_0$ in stress mode; computing a risk ratio $\sigma_{OR}/\sigma_{OB}^{cr}$ that is a risk ratio for stretch bending fracture, from the larger out of the stress $\sigma_{OR}$ and the fracture limit stress $\sigma_{OB}^{cr}$; and performing fracture determination for the element subject to determination based on the risk ratio $\sigma_{OR}/\sigma_{OB}^{cr}$.

According to the above aspect, fracture determination for the element subject to determination in the metal sheet is performed based on the risk ratio $\sigma_{OR}/\sigma_{OB}'$ obtained by the above calculation. Namely, the metal sheet can be determined to have fractured in cases in which the risk ratio $\sigma_{OR}/\sigma_{OB}'$ has reached 1.0, and determination can be made that the amount of leeway until the metal sheet fractures is less the closer the risk ratio $\sigma_{OR}/\sigma_{OB}^{cr}$ is to 1.0. Moreover, in the present mode, the fracture limit curve L2 is computed by correcting the fracture limit curve L1 obtained from uniaxial tensile testing with the above ratio $\gamma$, and the fracture limit stress $\sigma_{OB}^{cr}$ of the element subject to determination is determined according to the fracture limit curve L2. This thereby enables higher precision fracture determination to be performed on metal sheets than in cases in which the fracture limit stress of the element subject to determination is determined based on the fracture limit curve L1 obtained from uniaxial tensile testing alone.

A metal sheet bending fracture determination method according to a second aspect is the first aspect, further including: acquiring a characteristic bending-surface limit strain $\epsilon^0_\theta$ of the material configuring the metal sheet and converting the bending-surface limit strain $\epsilon^0_\theta$ into a bending-surface limit stress $\sigma_1^{cr}$; calculating a major strain $\epsilon_1$ of a surface plane corresponding to a bend outside of the element subject to determination, and converting from the major strain $\epsilon_1$ of the surface plane into a bending-surface major stress $\sigma_1$ using a relationship equation between equivalent stress and equivalent strain obtained by uniaxial tensile testing under the assumption of a static strain rate; calculating a first stress ratio $F1=\sigma_1/\sigma_1^{cr}$ that is a risk ratio of bending-surface cracking from the bending-surface limit stress $\sigma_1^{cr}$ and the magnitudes of the bending-surface major stresses $\sigma_1$; calculating a second risk ratio $\sigma_{OR}/\sigma OB^{cr}$ that is a risk ratio $\sigma_{OR}/\sigma_{OB}^{cr}$; comparing the first risk ratio $F1=\sigma_1/\sigma_1^{cr}$ to the second risk ratio $\sigma_{OR}/\sigma_{OB}^{cr}$ and determining which is larger out of the first risk ratio $F1=\sigma_1/\sigma_1^{cr}$ and the second risk ratio $\sigma_{OR}/\sigma_{OB}^{cr}$; performing fracture determination for the element subject to determination based on the first risk ratio $F1=\sigma_1/\sigma_1^{cr}$ in cases in which the first risk ratio $F1=\sigma_1/\sigma_1^{cr}$ was determined to be the larger; and performing fracture determination for the element subject to determination based on the second risk ratio $\sigma_{OR}/\sigma_{OB}^{cr}$ in cases in which the second risk ratio $\sigma_{OR}/\sigma_{OB}^{cr}$ was determined to be the larger.

According to the above mode, respective first risk ratios can be determined for bending fracture occurring under two different mechanisms: a fracture mode in which cracking occurs on the bend outside surface without the appearance of obvious localized necking; and a fracture mode in which fracture occurs after pronounced sheet thickness reduction (localized necking) has been observed at a bend leading end portion even though cracking does not occur at the bend outside.

A metal sheet bending fracture determination method according to a third mode is the second mode, wherein: the bending fracture limit stress $\sigma_{cr}$ is a true stress $\sigma_1$ that satisfies the following necking occurrence condition equation $$\frac{d\sigma_1}{d\varepsilon_1} = \sigma_1; \qquad [13]$$

and the fracture limit curve L1 is calculated by changing a constant $\alpha$ in the following equations to values of from 0 to 1

$$\sigma_1 = \frac{c}{\sqrt{1+\alpha^2}-\alpha}\left[\frac{4n(1-\alpha+\alpha^2)^{3/2}}{4-3\alpha-3\alpha^2+4\alpha^3}\right]^n \qquad [16]$$

$$\sigma_2 = \alpha\sigma_1. \qquad [17]$$

The above aspect enables the bending fracture limit stress $\sigma_{cr}$ and the fracture limit curve L1 to be obtained by performing a calculation based on the above calculation equation.

A metal sheet bending fracture determination method according to a fourth aspect is the first aspect or the aspect mode, wherein the fracture limit curve L1 is calculated by converting a fracture limit curve represented in space of strains measured from experiment into a fracture limit curve represented in space of stresses under the assumption of a static strain rate, or is calculated by converting a fracture limit curve in space of strains theoretically estimated from a stress-strain curve obtained from uniaxial tension into space of stresses under the assumption of a static strain rate.

The above mode also enables the fracture limit curve L1 to be obtained, similarly to the third mode.

Moreover, the metal sheet bending fracture determination may be performed by causing a computer to execute a computer program that executes the metal sheet bending fracture determination method of the first to fourth modes above.

A computer readable recording medium recorded with the computer program described above may also be produced.

Although explanation has been given regarding an exemplary embodiment of the invention above, the present invention is not limited to the above, and should be determined based on the recitation in the scope of claims.

The entire disclosure of Japanese Patent Application 2013-134199 filed on Jun. 26, 2013 is incorporated in the present specification by reference.

The invention claimed is:

1. A method of developing a vehicle body comprising:
   calculating, via a processing circuitry, a bending fracture limit stress for each of a plurality of bend amounts represented by (bend radius at sheet thickness center of a metal sheet)/(initial sheet thickness of the metal sheet);
   calculating, via the processing circuitry, a fracture limit curve for a uniform deformation state in space of stresses under the assumption of static strain rate and calculating a fracture limit stress under plane strain deformation, from work hardening characteristics obtained by uniaxial tensile testing of a material configuring the metal sheet;

determining, via the processing circuitry, a ratio between the bending fracture limit stress corresponding to (the metal sheet bend radius at sheet thickness center)/(the initial sheet thickness of the metal sheet) of an element subject to determination in the metal sheet and the fracture limit stress under plane strain deformation, and calculating, via the processing circuitry, a fracture limit curve corresponding to (the metal sheet bend radius at sheet thickness center)/(the initial sheet thickness of the metal sheet) by multiplying a stress component of the fracture limit curve in the uniform deformation state by the ratio between the bending fracture limit stress corresponding to (the metal sheet bend radius at sheet thickness center)/(the initial sheet thickness of the metal sheet) of the element subject to determination in the metal sheet and the fracture limit stress under plane strain deformation;

calculating, via the processing circuitry, a corresponding fracture limit stress from stress of the element subject to determination and the fracture limit curve corresponding to (the metal sheet bend radius at sheet thickness center)/(the initial sheet thickness of the metal sheet);

computing, via the processing circuitry, a risk ratio that is a ratio between the stress of the element subject to determination and the fracture limit stress calculated from the stress of the element subject to determination and the fracture limit curve corresponding to (the metal sheet bend radius at sheet thickness center)/(the initial sheet thickness of the metal sheet); and performing, via the processing circuitry, fracture determination for the element subject to determination based on the risk ratio, and developing a vehicle body based on the performed facture determination.

2. The method of developing the vehicle body of claim 1, further comprising:

acquiring, via the processing circuitry, a characteristic bending-surface limit strain of the material configuring the metal sheet, and converting the bending-surface limit strain into a bending-surface limit stress;

calculating, via the processing circuitry, a major strain of a surface plane corresponding to a bend outside of the element subject to determination, and converting from the major strain of the surface plane into a bending-surface major stress using a relationship equation between equivalent stress and equivalent strain obtained by uniaxial tensile testing under the assumption of a static strain rate;

calculating, via the processing circuitry, a first risk ratio that is a ratio between the bending-surface limit stress and the bending-surface major stress;

calculating, via the processing circuitry, a second risk ratio that is the risk ratio;

comparing the first risk ratio to the second risk ratio and determining, via the processing circuitry, which is larger out of the first risk ratio and the second risk ratio;

performing, via the processing circuitry, fracture determination for the element subject to determination based on the first risk ratio in cases in which the first risk ratio was determined to be the larger; and performing, via the processing circuitry, fracture determination for the element subject to determination based on the second risk ratio in cases in which the second risk ratio was determined to be the larger.

3. The method of developing the vehicle body of claim 1, wherein:

the bending fracture limit stress corresponding to (the metal sheet bend radius at sheet thickness center)/(the initial sheet thickness of the metal sheet) of the element subject to determination in the metal sheet is a true stress $\sigma_1$ that satisfies the following necking occurrence condition equation $$\frac{d\sigma_1}{d\varepsilon_1} = \sigma_1; \qquad [13]$$

and the fracture limit curve of the uniform deformation state is calculated by changing a constant $\alpha$ in the following equations to values of from 0 to 1

$$\sigma_1 = \frac{c}{\sqrt{1+\alpha^2-\alpha}} \left[ \frac{4n(1-\alpha+\alpha^2)^{3/2}}{4-3\alpha-3\alpha^2+4\alpha^3} \right]^n \qquad [16]$$

$$\sigma_2 = \alpha\sigma_1. \qquad [17]$$

4. The method of developing the vehicle body of claim 1, wherein the fracture limit curve of the uniform deformation state is calculated by converting a fracture limit curve represented in space of strains measured from experiment into a fracture limit curve represented in space of stresses under the assumption of a static strain rate, or is calculated by converting a fracture limit curve in space of strains theoretically estimated from a stress-strain curve obtained from uniaxial tension into space of stresses under the assumption of a static strain rate.

* * * * *